United States Patent
Balberg et al.

(10) Patent No.: US 9,131,880 B2
(45) Date of Patent: Sep. 15, 2015

(54) NONINVASIVE MEASUREMENTS IN A HUMAN BODY

(71) Applicant: OR-NIM Medical Ltd., Lod (IL)

(72) Inventors: Michal Balberg, Jerusalem (IL); Revital Pery-Shechter, Rishon-Lezion (IL)

(73) Assignee: OR-NIM MEDICAL LTD., Kfar Saba (IL)

( * ) Notice: Subject to any disclaimer, the term of this patent is extended or adjusted under 35 U.S.C. 154(b) by 107 days.

(21) Appl. No.: 13/849,943

(22) Filed: Mar. 25, 2013

(65) Prior Publication Data

US 2013/0317326 A1    Nov. 28, 2013

Related U.S. Application Data

(63) Continuation of application No. 10/593,318, filed as application No. PCT/IL2005/000300 on Mar. 16, 2005, now Pat. No. 8,423,116.

(51) Int. Cl.
*A61B 5/05* (2006.01)
*A61B 5/1455* (2006.01)
*A61B 5/145* (2006.01)
(Continued)

(52) U.S. Cl.
CPC ........... *A61B 5/1455* (2013.01); *A61B 5/14546* (2013.01); *A61B 5/14553* (2013.01); *A61B 5/7475* (2013.01); *A61B 8/0808* (2013.01); *A61B 8/4227* (2013.01); *G01S 15/8968* (2013.01); *A61B 8/06* (2013.01);
(Continued)

(58) Field of Classification Search
USPC ........................................ 600/407, 478, 476
See application file for complete search history.

(56) References Cited

U.S. PATENT DOCUMENTS 3,435,228 A    3/1969  Gordon
4,059,010 A    11/1977 Sachs
(Continued)

FOREIGN PATENT DOCUMENTS

DE    19654053    6/1998
EP    0549835     7/1993
(Continued)

OTHER PUBLICATIONS

A Communication together with an Annex to the Communication both dated Feb. 10, 2012, which issued during the prosecution of Applicant's European Patent Application No. 05 718 873.2.

(Continued)

*Primary Examiner* — Joel F Brutus
(74) *Attorney, Agent, or Firm* — Browdy and Neimark, PLLC

(57) ABSTRACT

Apparatus and methods are provided including directing acoustic radiation toward a region of interest within a subject's body. Light is transmitted from a light emitter to a light detector such that a first light portion is transmitted without passing through the subject's tissue, and a second light portion is transmitted via the region of interest. Scattered light of the second light portion contains a tagged component corresponding to photons tagged by the acoustic radiation, and an untagged component corresponding to photons untagged by the acoustic radiation. Light of the first light portion undergoes an interaction with light of the second light portion at the light detector. A property of tissue of the region of interest is determined, by decoupling from each other the tagged and untagged components of the second light portion, based upon the interaction between the light of the first and second light portions.

23 Claims, 16 Drawing Sheets

(51) Int. Cl.
*A61B 5/00* (2006.01)
*A61B 8/00* (2006.01)
*G01S 15/89* (2006.01)
*A61B 8/08* (2006.01)
*A61B 8/06* (2006.01)

(52) U.S. Cl.
CPC ...... *A61B 8/0816* (2013.01); *A61B 2562/0233* (2013.01); *A61B 2562/043* (2013.01)

(56) References Cited

U.S. PATENT DOCUMENTS

| | | | |
|---|---|---|---|
| 4,653,498 | A | 3/1987 | New et al. |
| 5,152,293 | A | 10/1992 | Vonesh |
| 5,193,543 | A | 3/1993 | Yelderman |
| 5,293,873 | A | 3/1994 | Fang |
| 5,299,570 | A | 4/1994 | Hatschek |
| 5,494,032 | A | 2/1996 | Robinson |
| 5,529,093 | A | 6/1996 | Gallagher |
| 6,002,958 | A | 12/1999 | Godik |
| 6,041,248 | A | 3/2000 | Wang |
| 6,047,602 | A | 4/2000 | Lynnworth |
| 6,240,309 | B1 | 5/2001 | Yamashita et al. |
| 6,264,610 | B1 | 7/2001 | Zhu |
| 6,456,862 | B2 | 9/2002 | Benni |
| 6,498,942 | B1 | 12/2002 | Esenaliev |
| 6,590,830 | B1 | 7/2003 | Garlick |
| 6,615,065 | B1 | 9/2003 | Barrett |
| 6,690,958 | B1 | 2/2004 | Walker |
| 6,738,653 | B1 | 5/2004 | Sfez et al. |
| 6,802,812 | B1 | 10/2004 | Walker |
| 6,815,694 | B2 | 11/2004 | Sfez et al. |
| 6,957,096 | B2 | 10/2005 | Sfez |
| 7,049,622 | B1 | 5/2006 | Weiss |
| 7,251,518 | B2 | 7/2007 | Herrmann |
| 7,747,301 | B2 | 6/2010 | Cheng |
| 8,108,022 | B2 | 1/2012 | Balberg |
| 8,126,524 | B2 | 2/2012 | Balberg |
| 8,423,116 | B2 | 4/2013 | Balberg et al. |
| 2002/0017141 | A1 | 2/2002 | Satoh |
| 2004/0099815 | A1* | 5/2004 | Sfez et al. .......... 250/492.1 |
| 2004/0127782 | A1 | 7/2004 | Sfez |
| 2005/0038344 | A1 | 2/2005 | Chance |
| 2008/0312533 | A1 | 12/2008 | Balberg |
| 2012/0184830 | A1 | 7/2012 | Balberg |

FOREIGN PATENT DOCUMENTS

| | | |
|---|---|---|
| EP | 549835 A1 | 7/1993 |
| EP | 1008326 | 6/2000 |
| EP | 1008326 A2 | 6/2000 |
| EP | 02/08740 | 1/2002 |
| WO | 98/50781 | 11/1998 |
| WO | 98/50781 A1 | 11/1998 |
| WO | 99/58060 | 11/1999 |
| WO | 99/58060 A1 | 11/1999 |
| WO | 02/08740 | 1/2002 |
| WO | 2006/097910 | 9/2006 |

OTHER PUBLICATIONS

An Office Action dated Nov. 5, 2010, which issued during the prosecution of U.S. Appl. No. 10/545,798.
An Office Action dated Nov. 3, 2010, which issued during the prosecution of U.S. Appl. No. 11/327,381.
An International Preliminary Report on Patentability dated Mar. 13, 2006, which issued during the prosecution of Applicant's PCT/IL2004/000835.
An International Search Report dated Mar. 4, 2005, which issued during the prosecution of Applicant's PCT/IL2004/000835.
An International Preliminary Report on Patentability dated Sep. 18, 2007, which issued during the prosecution of Applicant's PCT/IL2005/000300.
An Examination Report dated Aug. 21, 2009, which issued during the prosecution of European Patent Application No. 05718873.2.
An Examination Report dated Jun. 22, 2010, which issued during the prosecution of European Patent Application No. 04770506.6.
Communication dated Nov. 20, 2012 received during the prosecution of European Patent Application No. 05718873.
Notice of intention to grant patent dated Jan. 3, 2013 received during the prosecution of European Patent Application No. 05718873.
Report of telephone consultation dated Nov. 27, 2012 received during the prosecution of European Patent Application No. 05718873.
An Office Action dated Sep. 25, 2012, which issued during the prosecution of European Patent Application No. 05718873.
A Communication dated Jan. 27, 2011, which issued during the prosecution of Applicant's European Patent Application No. 05 718 873.2.
An Office Action dated Mar. 17, 2011, which issued during the prosecution of Applicant's U.S. Appl. No. 11/327,381.
An Office Action dated Apr. 13, 2011, which issued during the prosecution of Applicant's U.S. Appl. No. 10/545,798.
U.S. Appl. No. 60/502,212, filed Sep. 12, 2003.
U.S. Appl. No. 60/502,210, filed Sep. 12, 2003.
U.S. Appl. No. 60/553,142, filed Mar. 16, 2004.
U.S. Appl. No. 60/581,376, filed Jun. 22, 2004.
An Office Action dated May 8, 2012, which issued during the prosecution of Applicant's U.S. Appl. No. 10/593,318.
A Restriction Requirement dated Jan. 31, 2012, which issued during the prosecution of Applicant's U.S. Appl. No. 10/593,318.
A Notice of Allowance dated Jan. 7, 2013, which issued during the prosecution of Applicant's U.S. Appl. No. 10/593,318.
A Notice of Allowance dated Jun. 10, 2013, which issued during the prosecution of Applicant's U.S. Appl. No. 13/356,053.
A. Zourabian et al., "Trans-abdominal monitoring of fetal arterial blood oxygenation using pulse oxymetry", Journal of Biomedical Optics, vol. 5 No. 4, 2000, pp. 391-405.
Keinle et al., "In vivo determination of the optical properties of muscle with time-resolved reflectance using a layered model", Physics in Medicine and Biology (1999) vol. 44 pp. 2689-2702.
Leveque-Fort et al. "In situ local tissue characterization and imaging by backscattering acousto-optic imaging", Optics Communications vol. 196 (2001) pp. 127-131.
Lev a and G.B. Sfex "Direct, noninvasive detection of photon density in turbid media", Optics Letters (2002) vol. 27 No. 7 pp. 473-475. Abstract.
F. Rousseau et al. "Robust and Automatic Calibration Method for 3D freehad Ultrasound", Medical Image Computing and Computer Assisted Intervention, MICCAI'03, Nov. 2003.
Communication dated Nov. 20, 2012 received during the prosecution of European Patent Application No. 05718873 (3 pages).
Notice of intention to grant patent dated Jan. 3, 2013 received during the prosecution of European Patent Application No. 05718873 (82 pages).
Report of telephone consultation dated Nov. 27, 2012 received during the prosecution of European Patent Application No. 05718873 (3 pages).
An Office Action dated Sep. 25, 2012, which issued during the prosecution of European Patent Application No. 05718873. (5 pages).
A Communication together with an Annex to the Communication both dated Feb. 10, 2012, issued by the European Patent Office during the prosecution of copending European Patent Application No. 05 718 873.2 (6 pages).
An Office Action dated Nov. 5, 2010, which issued during the prosecution of U.S. Appl. No. 10/545,798 (30 pages).
An Office Action dated Nov. 3, 2010, which issued during the prosecution of U.S. Appl. No. 11/327,381 (27 pages).
An Examination Report dated Aug. 21, 2009, which issued during the prosecution of European Patent Application No. 05718873.2 (4 pages).
Balberg, U.S. Appl. No. 60/502,212, filed Sep. 12, 2003 (12 pages).
Balberg, U.S. Appl. No. 60/502,210, filed Sep. 12, 2003 (13 pages).
Balberg, U.S. Appl. No. 60/553,142, filed Mar. 16, 2004 (15 pages).
Balberg, U.S. Appl. No. 60/581,376, filed Jun. 22, 2004 (24 pages).
An Office Action dated Jan. 27, 2011, which issued during the prosecution of Applicant's European Patent Application No. 05 718 873.2.
Office Action dated May 31, 2010, issued in Israeli counterpart application PCT/IL05/000300.

* cited by examiner

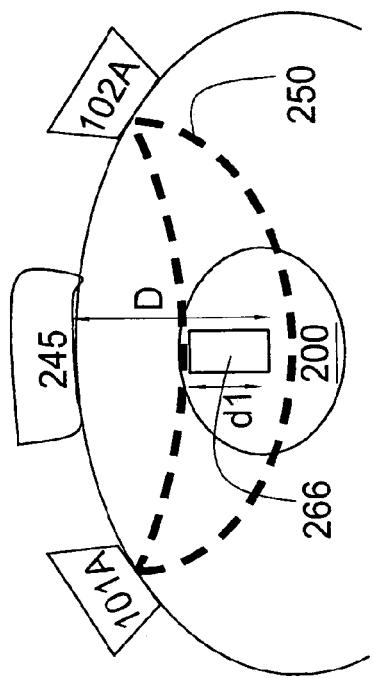
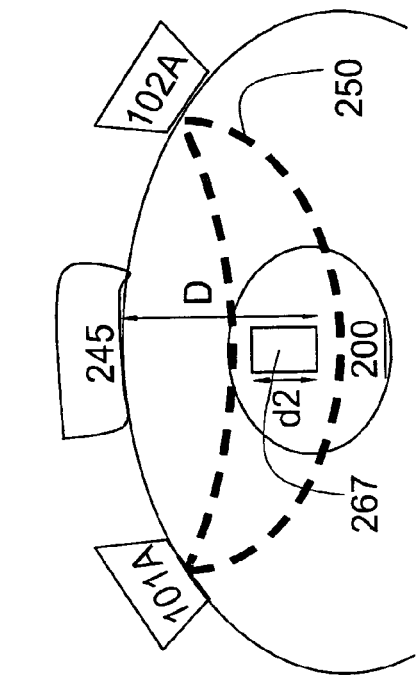
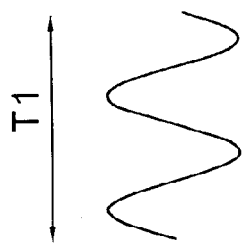
FIG. 2A
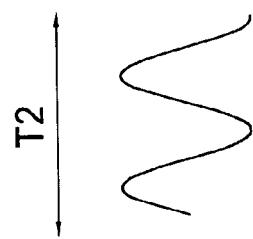
FIG. 2B

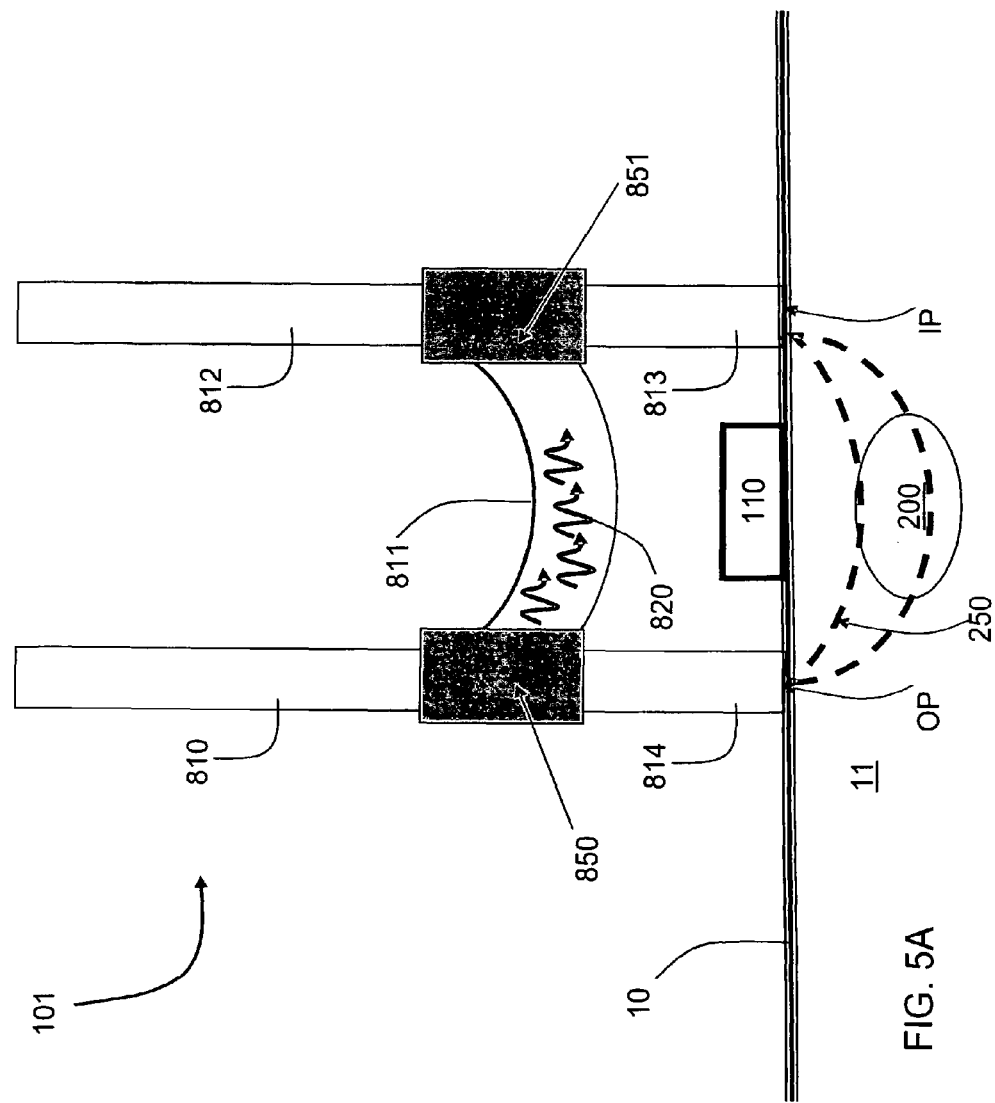

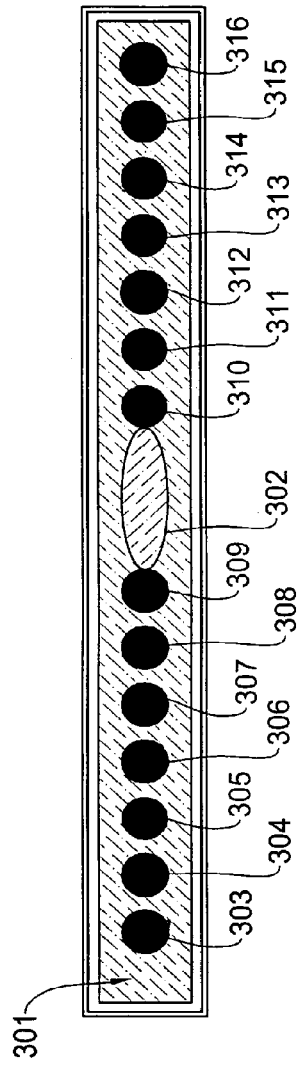
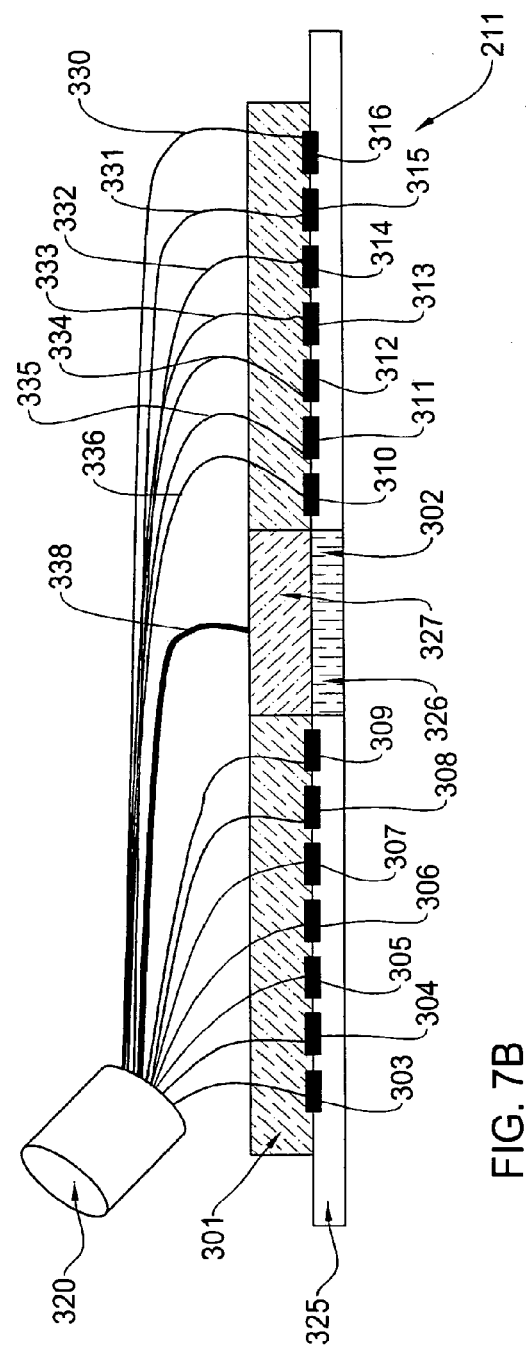

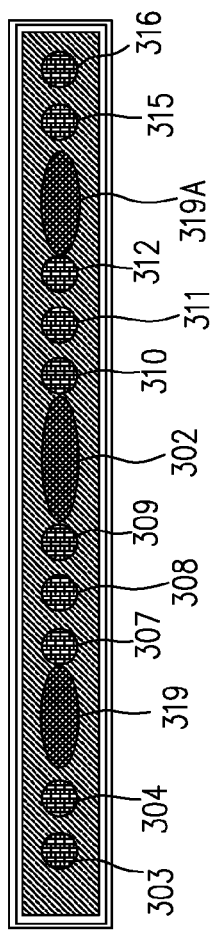
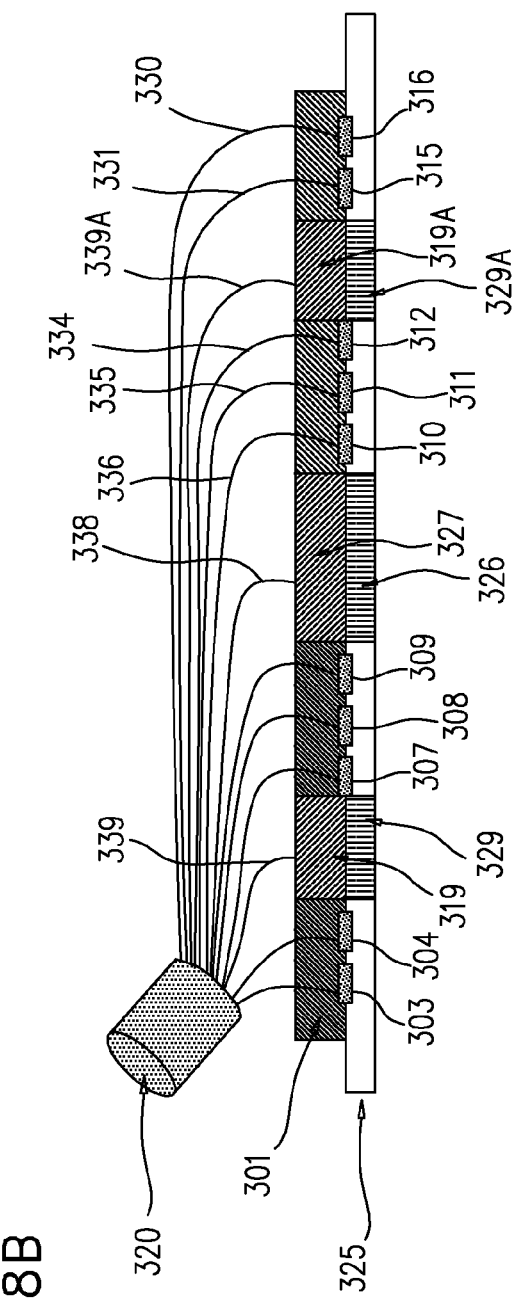
FIG. 8A
FIG. 8B

NONINVASIVE MEASUREMENTS IN A HUMAN BODY

FIELD OF THE INVENTION

This invention is generally in the field of medical devices, and relates to a method and system for noninvasive measurements in a human body. The invention is particularly useful for monitoring such parameters of the human body as oxygen saturation and/or concentration of analyte(s) in blood.

BACKGROUND OF THE INVENTION

Monitoring of the oxygenation level of a tissue region is required in order to determine if the tissue is viable or necrotic. For example, measuring the oxygen saturation level allows for determining whether a patient that experienced a stroke event should undergo a therapeutic procedure, whether a certain procedure is not necessary or whether performing certain procedures entails a high risk. Such measurements are also imperative for determining the efficiency of a treatment.

Near infrared light has been used to non-invasively probe the patient's brain based on different absorption characteristics of oxygenated and deoxygenated hemoglobin. However, near infrared spectroscopy (NIRS) suffers from several drawbacks associated for example with the fact that differential scattering of two different wavelengths used in the measurements result in an uncertainty in the path length that each wavelength passes; an inherent inability to localize the probed volume which requires computation-intensive tomographic devices and algorithms to resolve; analysis of the detected signal depends on a model being used to characterize the tissue structure being probed. This impedes the use of NIRS in real time medical settings.

U.S. Pat. No. 5,293,873 discloses a measuring arrangement for tissue-optical examination of a subject with visible, NIR or IR light. According to this technique, coherent light and ultrasound are directed at the subject along parallel propagation paths. The ultrasound causes a Doppler shift in the light emerging from the subject, this shift being related to certain tissue characteristics. The light emerging from the subject is detected and a corresponding signal is supplied to an evaluation stage which absolutely or relatively calculates the intensity of those parts of the detected light which proceeded through tissue not charged by ultrasound and those parts of the detected light which proceeded through tissue charged by ultrasound.

SUMMARY OF THE INVENTION

There is a need in the art to facilitate noninvasive measurements in a human body, by providing a novel method and system capable of monitoring blood or other fluid medium and/or tissue parameters in a human body, for example the concentration of an analyte in blood, fluid reservoirs or tissue regions. The technique of the present invention is capable of quantitatively monitoring cerebral oxygenation or blood volume so as to provide for example continuous information about the status of cerebral tissues for patients with a risk of neurological injuries.

The present invention utilizes the principles of ultrasound tagging of light. According to the present invention, tagging of light with acoustic radiation is used to enable distinguishing between the optical response of a region of interest (e.g., cerebral tissue, blood vessel) and regions outside the region of interest; and/or to significantly improve oximetry and pulse oximetry based measurements.

Thus, a body part is illuminated with at least one wavelength of light, and is irradiated with acoustic radiation (preferably ultrasound) such that the acoustic radiation overlaps with the illuminated region in the body (this overlapping volume is termed "tagged volume"). Light scattered from the body is appropriately detected. This scattered light includes photons tagged and untagged by the acoustic radiation.

According to the invention, an acoustic unit is operated with at least two different operating conditions, to thereby irradiate a certain region of a body part (region of interest) with acoustic radiation with at least one varying characteristic of said acoustic radiation. For example, the at least one variable characteristic is selected so as to provide at least two different effective optical pathlengths of the tagged photons scattered at the region of interest. A relation between measured data corresponding to the different conditions of the acoustic radiation (e.g., resulting in the different effective optical pathlengths) is indicative of a property of a tissue component in the region of interest.

The at least two different operating conditions of the acoustic unit (at least two different values of an acoustic radiation characteristic) may be selected so as to irradiate different volumes of the region of interest (i.e., the different tagged volumes substantially overlap in space), and/or to provide different tagging efficiencies. The irradiation of different volumes can be achieved by generating pulses of acoustic radiation having different duration and/or generating acoustic radiation of different beam waists. The different tagging efficiencies can be obtained by generating pulses of acoustic radiation having different amplitude and/or frequency and/or gradient of chirping.

It should be noted that the term "property of a tissue" used herein signifies at least one parameter of a medium or media in a region of interest, where the media may include fluid or any other tissue.

The term "effective optical pathlength" signifies an optical pathlength from an illumination assembly (its light output port) to a detection assembly (its light input port) which accounts for tissue scattering.

The term "tagging efficiency" signifies a number of tagged photons relative to a number of untagged photons scattered by scattering centers inside a tagged volume.

The term "different volumes" or "different tagged volumes" refers to volumes substantially within the same location relative to the acoustic transducer arrangement, namely volumes that substantially overlap in space, such that the average optical and acoustic characteristics of the tagged volumes are about the same during and in between the different measurements; therefore the relative change in the tagged volume between the two measurements is smaller than the tagged volume.

Preferably, a body part (e.g., a human head) containing a region of interest (e.g., cerebral tissue) is illuminated with light (e.g., of at least two different wavelengths) and is irradiated with acoustic radiation, in a manner to ensure optimal operating condition for measurements. This optimal operating condition is such that the illuminating light and acoustic radiation overlap within the region of interest and thus light scattered from the region of interest is "tagged" by acoustic radiation (the light is modulated by the frequency of the acoustic radiation) while substantially do not overlap in a region outside the region of interest. Moreover, the optimal operating condition is such as to ensure that detected light includes a portion of light scattered by the region of interest and tagged by acoustic radiation, and a portion of untagged light scattered by regions outside the region of interest. This allows for distinguishing between the light responses of the region of interest and its surroundings (e.g., cerebral and extracranial tissues; a vascular cavity and surrounding tissues; or a blood pool and surrounding tissues).

It should be understood that acoustic radiation may be in the form of continuous waves, or pulses- or bursts-based acoustic radiation.

The technique of the present invention can be used in pulse oximetry measurements for determining oxygen saturation level in a region of interest. Comparing the technique of the present invention to pure pulse oximetry measurements that are highly sensitive to minor movements of a body, measured data obtained by the technique of the present invention, being for example in the form of a power spectrum of a tagged light response of the region of interest, is practically insensitive to movements of regions outside the region of interest.

Preferably, measured data is in the form of time dependent and/or wavelength dependent variations of the tagged light signals for at least two wavelengths of illuminating light.

The present invention provides for non-invasively determining such parameters as oxygen saturation level in the region of interest, concentration of a substance (e.g. blood, hemoglobin) or a structure within the region of interest, the presence and concentration of lamellar bodies in amniotic fluid for determining the level of lung maturity of the fetus, the presence and/or concentration of meconium in the amniotic fluid, presence and/or concentration of blood in the amniotic fluid; as well as for noninvasive monitoring the optical properties of other extravascular fluids such as pleural, pericardial, peritoneal (around the abdominal and pelvis cavities) and synovial fluids.

According to the invention, acoustic (ultrasound) radiation used for measurements may or may not be focused, since the measurements utilize ultrasound tagging for the purposes of distinguishing between light responses of the region of interest and its surroundings and/or for increasing signal to noise ratio of ultrasound tagging based measurements, while not necessarily for imaging. The invention may also be used for imaging of a body part, namely, for mapping the optical attenuation of the body tissues. This is implemented by appropriately operating optical and acoustic units.

The present invention may utilize the principles of oximetry for processing the measured data. To this end, the illumination with at least two different wavelengths is applied. In some embodiments, the light response signals are collected over a time period larger than a heart beat, and the principles of pulse oximetry are used to determine the oxygen saturation level.

The present invention may be used to measure the concentration of a substance in a body region using illumination with at least a single wavelength. In some embodiments, the wavelength is selected to correspond to a characteristic wavelength being selectively absorbed or scattered by the substance. For example, the redox state of cytochrome-c oxidase can be monitored at a wavelength (or a selection of wavelengths) being indicative of oxygen availability and metabolic activity of the tissue. As another example, potassium depolarization is affected by hypoxia. Thus, measurement of potassium related optical changes is an indirect indicator of changes in oxygenation. Contrast agents, such as indocyanine green (ICG) can also be monitored using the technique of the present invention, where the contrast agent is administered through blood vessels that perfuse the region of interest, both the dynamics of changes in the concentration of the contrast agent and the absolute concentration can be determined. Other tissue analytes such as bilirubin, glucose and urea, can be monitored using appropriate selection of wavelengths for illumination.

Preferably, a measurement unit (an illumination assembly, a light detection assembly, and an acoustic transducer arrangement) is placed in close contact with the respective body portion (e.g., the skin overlaying the skull). As indicated above, the illumination assembly is configured and operable to illuminate the body portion with at least two wavelengths. The acoustic transducer arrangement is configured and operable to transmit acoustic radiation into the same volume from which the light detector collects scattered light.

The light detection assembly may be oriented for collecting both back scattered light and forward scattered light.

The present invention preferably utilizes imaging of a region of interest prior to or concurrently with applying measurements thereto. This is in order to assist in determining an optimal positioning of a measurement system (its probe device) to provide the optimized operating condition for measurements. The imaging may be implemented using ultrasound, magnetic resonance (MR), computed tomography (CT) or positron emission tomography (PET). If ultrasound-based imaging is used, it can be implemented either using or not the same ultrasound transducer arrangement that is used for measurements.

Preferably, the invention also provides for using ultrasound radiation for determining such parameters of blood in the region of interest as blood flow, tissue velocity profile, etc. To this end, reflections of ultrasound radiation from the irradiated region are analyzed using any known suitable Doppler-based techniques. The incident ultrasound radiation may be in the form of continuous waves or pulses (gates).

There is thus provided according to one broad aspect of the present invention, a measurement system for use in non-invasive measurements on a human body, the system comprising:

a measurement unit comprising an optical unit having an illumination assembly and a light detection assembly; and an acoustic unit for generating acoustic radiation; the measurement unit being configured and operable to provide an operating condition such that the acoustic radiation overlap with a certain illuminated region in the body, and that the detection assembly collects light scattered from said certain region, measured data generated by the detection assembly being thereby indicative of scattered light having photons tagged and untagged by the acoustic radiation, thereby enabling to identify a light response of said certain region to illuminating light;

a control unit connectable to the optical unit and to the acoustic unit, the control unit being preprogrammed to operate the acoustic unit with at least two different operating conditions to vary at least one characteristic of acoustic radiation, the control unit being responsive to the measured data and preprogrammed to process and analyze the measured data to extract therefrom a data portion associated with the light response of said certain region, thereby enabling determination of a property of a tissue component in said certain region based on a relation between the measured data corresponding to the at least two different operating conditions of the acoustic unit.

According to another broad aspect of the invention, there is provided a method for use for non-invasive measurements in a human body, the method comprising: applying acoustic radiation to a certain illuminated region in the body, with at least two different conditions of the applied radiation achievable by varying at least one characteristic of the acoustic radiation; detecting light scattered from the body part and generating measured data indicative of detected photons tagged and untagged by the acoustic radiation; analyzing the measured data to extract therefrom a data portion corresponding to the tagged photons and being therefore associated with a light response of said certain region, to thereby enable determination of tissue properties of said certain region based on a relation between the measured data portions corresponding to the at least two different operating conditions.

According to yet another broad aspect of the invention, there is provided a probe device for use in a system for monitoring tissue properties in a human body, the probe comprising: a support structure configured to contact a body portion, said support structure carrying an array of at least two light output ports arranged in a spaced-apart relationship and being connectable to a light source assembly, an array of light input ports arranged in a spaced-apart relationship and being connectable to a light detection assembly, and at least one acoustic output port of an acoustic unit, the arrangement of the light ports and the acoustic port being such as to allow selection of at least one of said light output ports, at least one of the light input ports and at least one of the acoustic output ports such that acoustic radiation of a predetermined frequency range coming from said at least one selected acoustic output port and illuminating light coming from said at least one selected light output port overlap within a region of interest in the body, and in that said at least one light input port collects light scattered from the overlapping region and light scattered from outside the region of interest.

BRIEF DESCRIPTION OF THE DRAWINGS

In order to understand the invention and to see how it may be carried out in practice, preferred embodiment will now be described, by way of non-limiting examples only, with reference to the accompanying drawings, in which:

FIGS. 2A and 2B schematically illustrate the principles of a measurement scheme according to an example of the invention;

FIGS. 5A and 5B schematically illustrate two examples of configuration of a measurement unit suitable to be used in the system of the present invention to carry out detection of required parameter(s) of a region of interest using a local oscillator method;

FIGS. 7A-7B and 8A-8B exemplify various configurations of a support structure (probe) of the present invention carrying at least part of a measurement unit.

DETAILED DESCRIPTION OF THE INVENTION

Figure 1A:
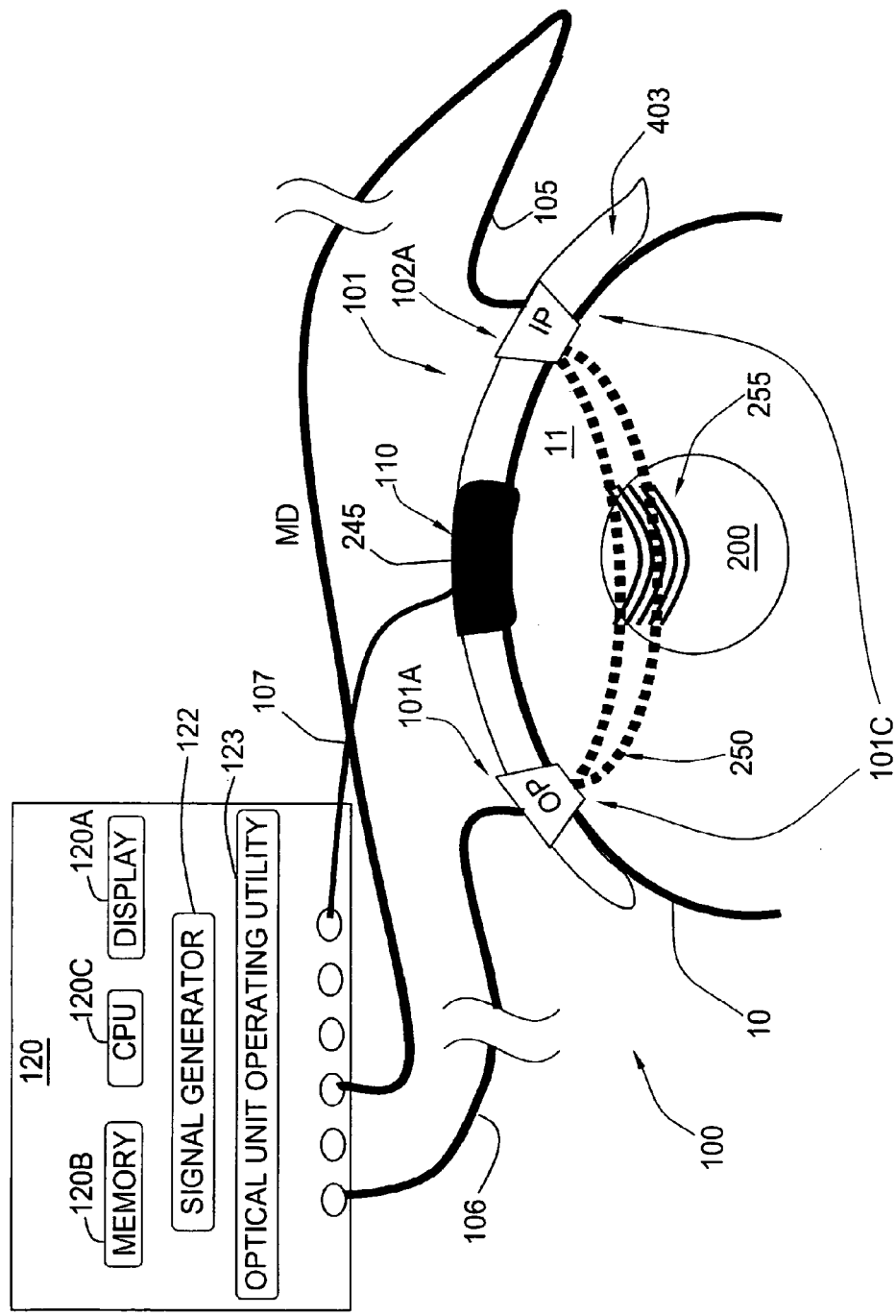
FIGS. 1A to 1C schematically illustrate three different examples, respectively, of a monitoring system according to the invention for monitoring a region of interest in a human or animal body.
Figure 1B:
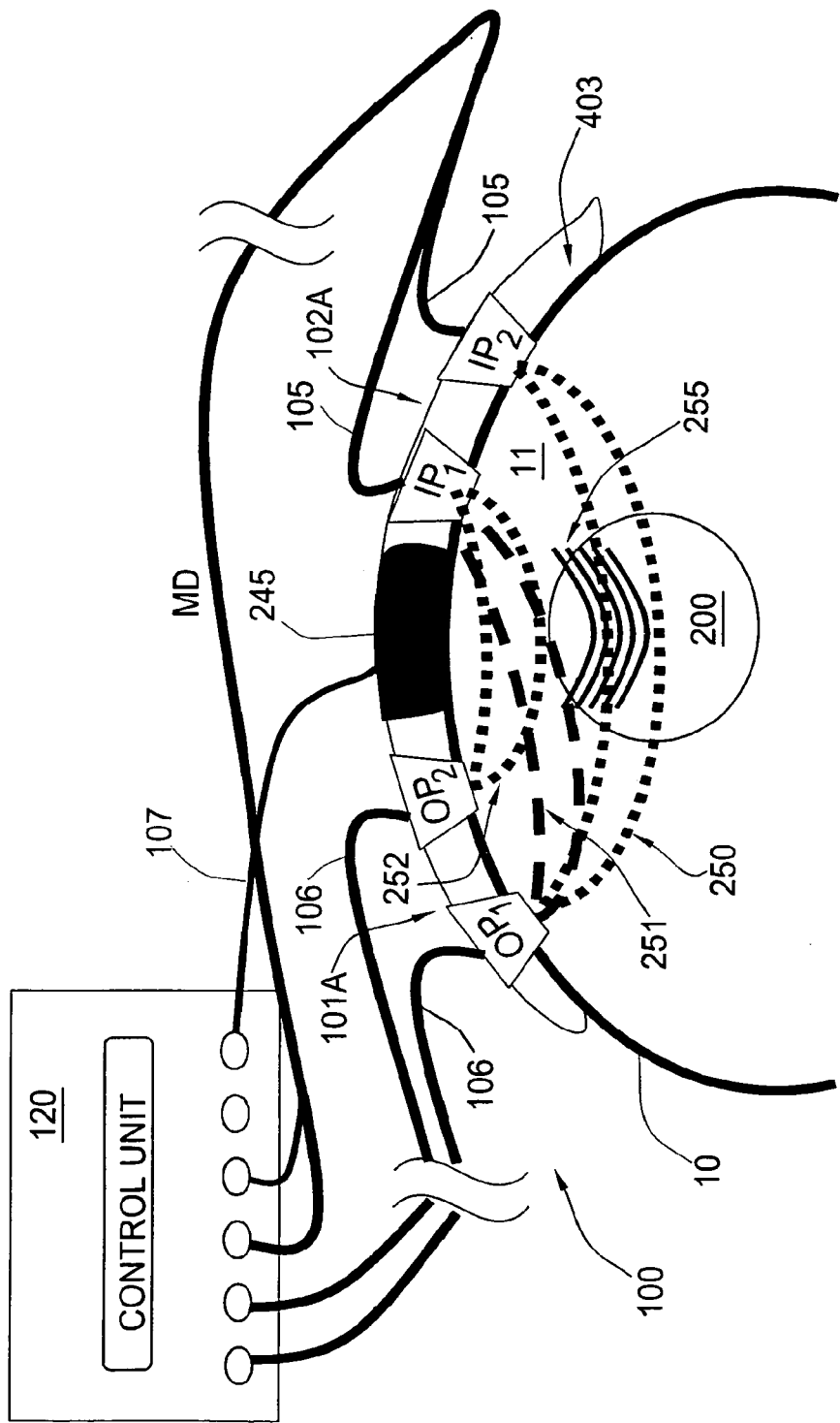
Figure 1C:
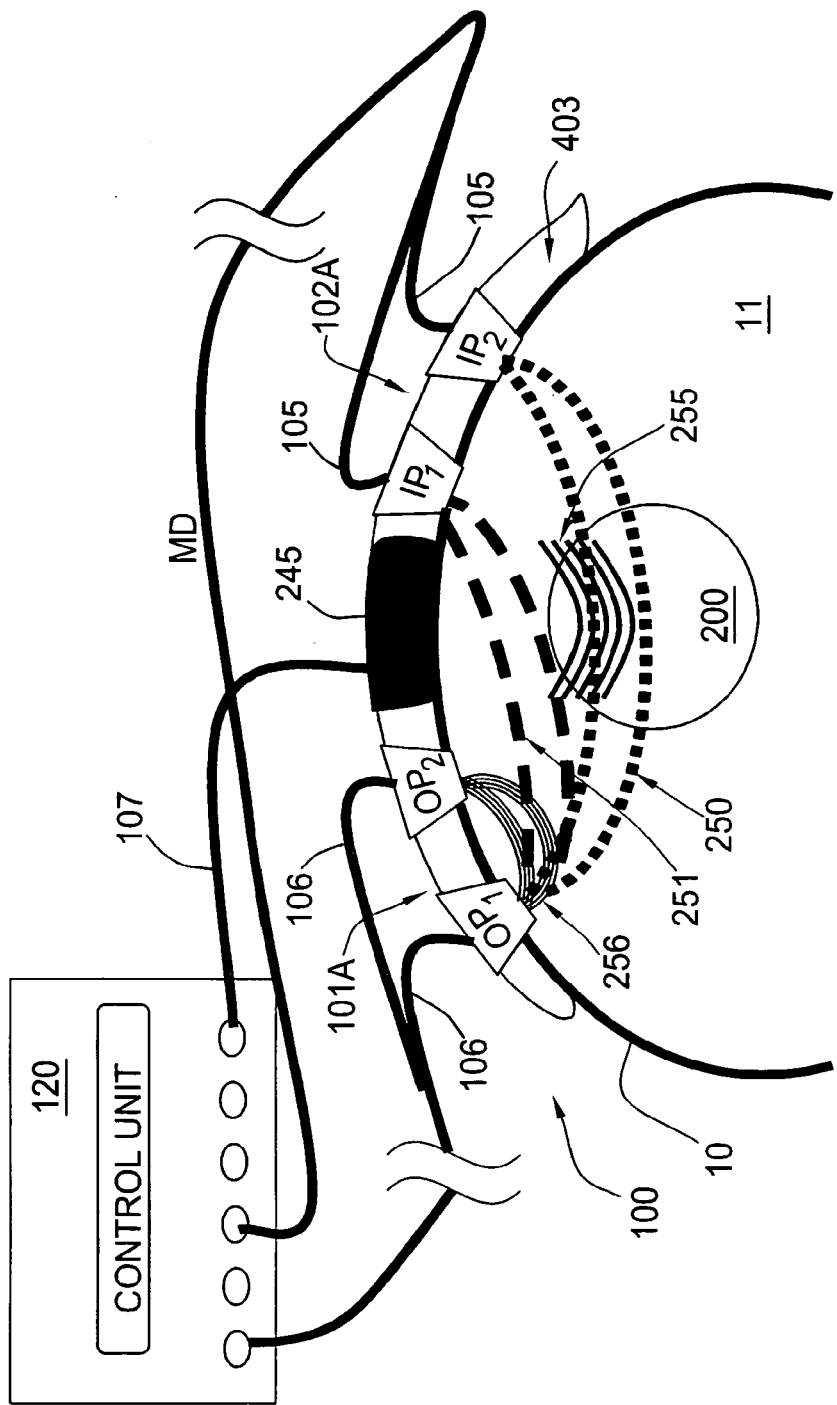

Reference is made to FIGS. 1A-1C illustrating schematically three specific but not limiting examples of a measurement system, generally designated 100, configured and operable according to the invention for non-invasive measurements of one or more parameters (properties of tissue components) of a region of interest 200 in a human or animal body. This may be an oxygen saturation level, or various other parameters such as the concentration of an analyte in the patient's blood, or the perfusion of an analyte/metabolite in tissues. To facilitate understanding, the same reference numbers are used for identifying components that are common in all the examples of the invention.

The system 100 includes a measurement unit 101 and a control unit 120. The measurement unit 101 includes: an optical unit 101C formed by an illumination assembly 101A and a light detection assembly 102A; and an acoustic unit formed by a transducer arrangement 110. The control unit 120 is configured to control the operation of the measurement unit 101 and to process and analyze measured data generated by the measurement unit 101.

The illumination assembly 101A may include one or more illuminator units associated with one or more locations, respectively, with respect to the region of interest. Similarly, the detection assembly 102A may include one or more detector units associated with one or more detecting locations, respectively. The illuminator unit may include one or more lighting elements; as well as the detector unit may include one or more light detecting elements. The lighting element is formed by a light emitter and possibly also a light guiding unit (e.g., an optical fiber or fiber bundle); the light detecting element is formed by a light sensor and possibly also a light guiding unit (e.g., optical fiber or fiber bundle).

In the example of FIG. 1A, the illumination assembly 101A includes a single illuminator unit, and the light detection assembly 102A includes a single detector unit. This does not necessarily signify a single illuminating element and/or a single detecting element, but may refer to an array of illuminating element provided they are associated with the same location with respect to the region of interest, and/or an array of detecting element associated with the same location relative to the region of interest.

The optical unit 101C and the acoustic unit 110 are connectable to the control unit 120 via wires or wireless means. The control unit 120 is typically a computer system including inter alia a power supply unit (not shown); a control panel with input/output functions, a data presentation utility (display) 120A; a memory utility 120B; and a data processing and analyzing utility (e.g. CPU) 120C. Also provided in the control unit 120 are a signal generator (e.g. function generator and phase control) 122 configured and operable to control the operation of the transducer arrangement 110, and an appropriate utility 123 configured for operating the optical unit 101C. The CPU 120C is preprogrammed for receiving measured data MD coming from the detection assembly 102A and for processing this data to determine desired parameter(s) of the region of interest, e.g., oxygen saturation level.

In the present examples, the measurement unit 101 is configured as a probe having a support structure (preferably flexible) 403 to be put on the body part to be measured. The support structure 403 carries at least part of the illumination assembly 101A (at least one light output port—single output port OP in the example of FIG. 1A and multiple ports in examples of FIGS. 1B-1C) and at least part of the detection assembly 102A (at least one light input port—single input port IP in the example of FIG. 1A and multiple ports in examples of FIGS. 1B-1C).

It should be understood that the light output port OP may be integral with the light emitting element(s) or may be constituted by a distal end of an optical fiber unit connected at its other end to light emitting element(s) located outside the support structure (e.g., at the control unit). Similarly, the light input port IP may be integral with the light detecting element(s) or may be constituted by a distal end of an optical fiber unit which by its other end is connected to light detecting element(s) located outside the support structure (e.g., at the control unit).

Generally, the illumination assembly 101A can be configured to produce light of a single wavelength. Preferably, the illumination assembly 101A is configured for generating light of at least two different wavelengths. To this end, the illumination assembly may include at least two light emitters (e.g., laser diodes), for example one emitting narrow bandwidth photons of a wavelength within the range of 605 nm to 805 nm and the other emitting photons of a wavelength within the range of 800 nm to 1300 nm; or may include a broadband light source. The illumination assembly 101A may for example be preprogrammed to produce the different wavelength components at different times, or simultaneously produce wavelength components with different frequency- and/or phase-modulation. Accordingly, the control unit 120 is preprogrammed to identify, in a signal generated by the detection assembly 102A, the corresponding wavelength of the irradiating light, using time, and/or phase and/or frequency analysis. The detection assembly may include an appropriate frequency filter.

Thus, the illumination assembly 101A may include light emitter(s) carried by the support structure 403 and communicating with the control unit 120 using wires 106 or wireless signal transmission. Alternatively, the light emitter(s) may be located outside the support structure 403 (e.g., within the control unit 120) and connector 106 is constituted by a light guiding assembly (e.g., optical fibers) for guiding light to the light output port OP located on the support structure 403.

The detection assembly 102A includes one or more light detectors. This may be a photomultiplier tube, photodiode, avalanche photodiode, or preferably an image pixel array, e.g., CCD or an array of photodiodes. The detector(s) may be accommodated outside the support structure (probe) 403, e.g., may be located within the control unit 120, and returned light (light response) may be guided from the input port IP of the detection assembly via light guiding means 105 (e.g., optical fibers). Alternatively, the detector(s) may be located at the support structure and connector 105 is configured to connect an electrical output of the detector(s) indicative of measured data MD to the control unit 120.

It should also be understood that connectors 105 and 106 may be electric wires connecting the control unit 120 to the illumination assembly and detection assembly located on the probe 403, or the connection may be wireless.

Thus, generally, the terms "illumination assembly" and "detection assembly" as carried by a support structure which is brought in contact with a body part to be measured, are constituted by at least light transmitting and receiving ports.

It should be noted that, for the purposes of the present invention, the light input port of the detection assembly 102A can be larger than that used for imaging by means of diffuse light. In diffuse light imaging, localization is achieved by small input ports; otherwise light from a large volume is collected. According to the invention, light collection from a large volume is desired, since localization is achieved by the ultrasound tagging. Hence, the input port of the detection assembly 102A is optimized to collect light from a substantially large volume of tissue and/or blood, for example by using large area detectors or CCD cameras or an array of detectors comprising a single input port.

As indicated above, the detection assembly 102A may include two separate detectors or an array of detectors. Each detector may be coupled to a bandpass filter configured for transmitting light of a corresponding one of the wavelengths produced by the illumination assembly 101A. The bandpass filters may include high-pass, low-pass and bandpass optical filters. Alternatively narrow bandwidth detectors can be used.

The transducer arrangement 110 may be located on the support structure 403 and connected to the control unit 120 (its signal generator 122 and CPU 120C) using cables and/or optical fibers 107 and/or using wireless means. Alternatively, connector 107 may constitute an acoustic guiding unit for connecting the transducer(s) located outside the supports structure (e.g., at the control unit 120) to an acoustic output port 245 on the support structure.

In the case actual light detectors are placed on the flexible support structure (probe) 403, the detectors are preferably mechanically and electronically isolated such that acoustic waves propagating from the acoustic output port 245 minimally affect the collection of photons by the detectors and the transduction of light signals into electronic signals. If the ultrasound transducer arrangement 110 is also placed on the probe 403, then the configuration is such as to prevent RF and other electronic signals generated by the transducer arrangement from interfering with the collection of photons by the detectors and with the transduction of light signals into electronic signals. This is implemented using a shielding arrangement, for example including electrical isolation of the detectors by appropriate materials that are poor conductors, or by creating a Faraday cage around the detectors (detecting elements), or creating mechanical isolation by using appropriate materials that attenuate the propagation of sheer acoustic waves through the probe itself or through the body tissues. As indicated above, detectors may be connected to the probe 403 using connecting ports (possibly detachable). The connecting ports are configured to isolate mechanical and electrical signals at the frequencies generated by the ultrasound transducer arrangement and at other frequencies.

The transducer arrangement 110 may be a single acoustic element, configured and operable for emitting focused or unfocused acoustic beams or emitting acoustic pulses; or a piezoelectric phased array capable of producing acoustic beams with variable direction, focus, duration and phase; or may be an array of silicon units or other pressure generating units configured as a single element or an array of elements (phased array); or a complete ultrasound imaging probe comprising transmitting and receiving units. The transducer arrangement may be connected to an amplifier (not shown) located within the control unit 120 and operable to amplify electronic signals generated by the signal generator 122. The control unit is preprogrammed to operate the transducer arrangement 110 (via the signal generator 122) in a predetermined manner as will be described below.

In addition, the transducer arrangement 110 may include an array of laser generated ultrasound elements (LGU) coupled to a laser source capable of emitting short pulses of light (e.g., of the order of 10 nsec-100 μsec). These short pulses of light are transmitted to the transducer arrangement 110 via optical fibers to produce acoustic waves at a desired frequency, time and duration. The onset of light pulses emitted in each element may experience a relative time delay between the elements. This delay creates a phase delay between the generated acoustic waves at each element and can be used to focus or stir the generated beams towards a desired location (i.e. the region of interest 200). Elements for laser generated ultrasound transducers are known in the art, for example such as disclosed in PCT application WO03057061. Using such a transducer arrangement will make the probe 403 cheaper, since the elements of the probe are optical fibers. When LGU elements are used, the control unit 120 controls the activation of laser sources emitting short pulses to create acoustic waves, in accordance with an embodiment of the present invention, referring to the activation of the signal generator. For example, the control unit 120 may activate the lasers such that they emit a series of short pulses consecutively in order to create a specific duration of acoustic bursts; or control unit 120 may control the amplitude of the laser pulses, such that the amplitude of the acoustic waves generated by the LGU elements is determined according to a specific embodiment of the invention as will be described below.

The detection assembly 102A generates electronic signals in response to the amplitude and phase of photons reaching the input port IP. These electronic signals may be filtered by analog or digital filters, for example bandpass filters, that are appropriately provided being connected to the data processing utility 120C of the control unit 120 or being a part of this processing utility. The bandwidth of these filters can be fixed or changed by the control unit 120. The bandwidth tuning can be performed optically by heterodyne detection or by using a plurality of filters having different bandwidths, or by tunable filters which are coupled to each detector. Alternatively, filters can be electronic. Preferably, prior to performing the actual measurements, an optimal positioning of the assemblies of the optical unit and of the acoustic unit with respect to region of interest 200 is provided to satisfy an operating condition for measurements. The operating condition is such that both the illuminating light 250 (at least a portion thereof) and the acoustic radiation 255 irradiate the same region (volume) simultaneously, while substantially not overlapping in outside regions; and that the detection assembly detects light scattered from the region of interest 200 and regions outside thereof. Generally speaking, the positioning of the optical unit and transducer arrangement with respect to the region of interest 200 is such as to enable to distinguish between scattered photons collected from region 200 and regions 11 outside this region, using acoustic tagging of light. As will be described further below, the region of interest may be identified by the control unit 120.

As indicated above, the pre-positioning may be carried out using an ultrasound imaging. An imaging system of any known suitable configuration may be used, which may utilize the same transducer arrangement 110 used for the measurement process or another ultrasound transducer(s). Ultrasound images of a body part containing the region of interest 200 are acquired and analyzed by the control unit 120 (which in this case is installed with a suitable image processing utility) or another appropriately preprogrammed computer system, to determine the optimal positioning of the optical unit 101 (namely the illumination assembly 101A and the detection assembly 102A) relative to the region of interest and relative to the acoustic unit 110.

The illumination assembly 101A is preferably placed at the shortest distance to the region of interest 200. Preferably, the illumination assembly 101A is placed such that a light path between the illumination assembly 101A and the region 200 is that suffering the least attenuation at the wavelengths chosen for measurements, as compared to the other paths. A distance between the illumination assembly 101A and the detection unit 101B is preferably determined to be at least equal to and preferably larger than a distance between the illumination assembly 101A and region 200.

Preferably, the support structure 403 is configured to define various positions for attaching the detection assembly 102A and/or the illumination assembly 101A to be at the correct distance between them. For example, these positions may be determined by using a sliding bar (not shown) that is attached to the light detection assembly 102A and can be secured to the support structure 403 using a small screw or a latch. Alternatively, a plurality of light output ports and/or plurality of light input ports are provided on the support structure 403 and the control unit 120 operates to select the appropriate light source (s) and detector(s) (light output port and light input port) for measurements. This selection is based on the signals generated by each detector and on the geometry of the body part and the position of the region of interest therein.

Additionally, the illumination assembly 101A and the detection assembly 102A are placed such that the light output port OP of the illumination assembly and the light input port IP of the detection assembly are in close contact with an outer skin 10 of the body part. Optionally, an index matching oil or adhesive is used to reduce reflection of light from the outer skin 10. The adhesive may be used to secure the support structure 403 to a specific location on the body part. Alternatively, or additionally, a belt can be used to prevent movement of the support structure 403.

Once the position of the illumination and detection assemblies is fixed, the acoustic transducer arrangement 110 is positioned such that acoustic waves 255 generated by the transducer arrangement 110 are coupled into the appropriate body part, propagate therethrough and reach the region of interest 200. For example, in the case the illumination and detection assemblies are appropriately placed to illuminate and collect light scattered by region 200, the transducer arrangement 110 is placed such that acoustic waves 255 propagate through the same part of region 200 from which scattered photons 250 are detected by the detection assembly 102A. The transducer arrangement 110 may be fixed to an appropriate location using an ultrasound transmitting adhesive or acoustic coupling material (such as gel or a hydrogel adhesive, or ultrasound compatible glue), and optionally a belt for fixing the transducer to one location. The ultrasound transducer arrangement 110 may be configured as a phased array transducer producing a focused beam that is being scanned over a region of skin 10 overlaying the body part.

Having optimally positioned the illumination and detection assemblies and the acoustic transducer arrangement, measurements are taken by appropriately operating the measuring unit 101. The control unit 120 actuates the illumination assembly 101A to generate photons 250 (preferably of at least two different wavelengths). The illumination assembly 101A may be configured and operable to produce a continuous stream of photons 250 (CW), or a time modulated stream (at a certain frequency W), or a train of pulses. Photons 250 propagate through the body part and reach region 200. A portion of photons 250 is absorbed by region 200 and a portion of photons 250 is scattered by this region 200 and by its surroundings 11. A portion of the scattered photons 250 propagates through the body part (surroundings of the region of interest) and reaches the detection assembly 102A. The latter collects at least a part of these photons and generates measured data MD indicative thereof, i.e., an electric signal in response to the number of photons that are collected at the input port IP of the detection assembly at a specific point in time for each irradiating wavelength generated by the illumination assembly 101A.

It should be noted that, in the case the detection assembly 102A is spaced from the illumination assembly 101A a distance equal to or larger than twice the minimal distance between the region 200 and the illumination assembly 101A, the detection assembly 102A collects both back and forward scattered photons. In the case the illumination assembly 101A includes a laser with a coherence length larger than the optical path of scattered photons in the tissue, an interference pattern resulting in a speckle image is generated on the input port IP of the detection assembly. In order to detect and analyze the speckle image, the detection assembly 102A may include an array of detectors with an individual size comparable to that of individual speckle.

Figure 1D:
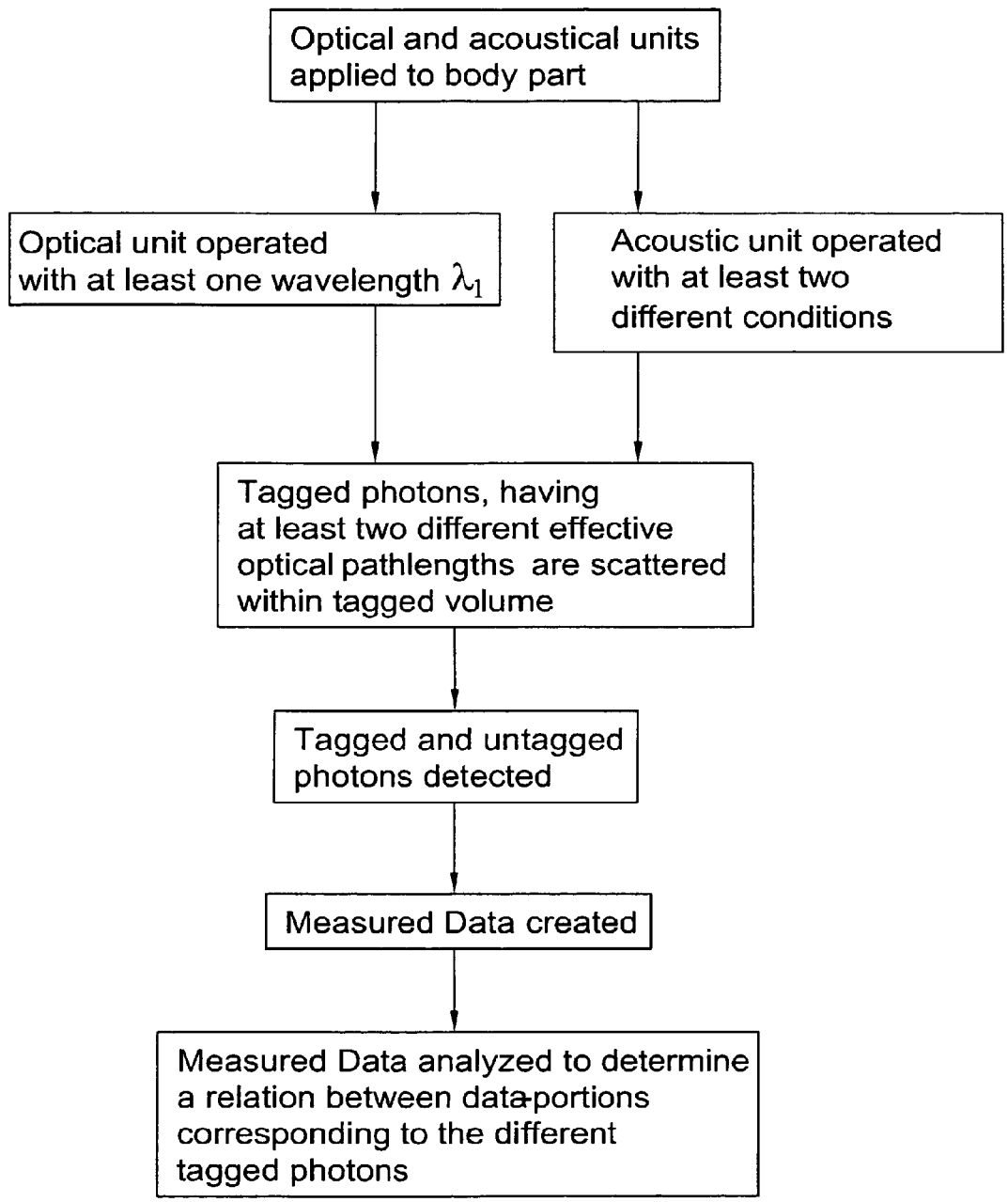
FIG. 1D is a flow diagram of a method of the present invention.

FIG. 1D illustrates a flow diagram of the main steps in a method of the present invention for measurement in a human body. The optical and acoustic units are appropriately applied to the body. The optical unit is operated (by the control unit) to illuminate the body with at least one wavelength. As photons 250 illuminate region 200, the transducer arrangement 110 is operated with at least two different operating conditions defined by varying at least one characteristic of acoustic radiation 255. Acoustic radiation propagates through the body to irradiate a volume of region 200 from which scattered photons 250 are detected by the detection assembly 102A. The tagged volume corresponds to this acoustically irradiated volume at the measurement time. The interaction of acoustic waves 255 with photons 250 results in that the frequency of photons 250 is shifted by the frequency of acoustic waves 255. In addition, photons 250 scattered within the tagged volume experience a modulation of the optical pathlength resulting from modulation of the density of scattering centers and from their acoustic induced motion. Acoustic radiation operated with at least two different conditions irradiates the tagged volume. The two conditions correspond to two different effective optical pathlength of tagged photons scattered within the tagged volume. The effective optical pathlengths depends on the volume of the tagged volume and/or on changes in the tagging efficiency of photons scattered within the tagged volume. The detection assembly 102A detects the modulated photons ("tagged photons") and the unmodulated photons at the original frequency ("untagged photons") at the two measurement conditions, for each of the illuminating wavelengths. The detection assembly 102A generates measured data MD (electric signals) indicative of the detected photons. The measured data portion corresponding to the tagged photons is termed "tagged signal".

Figure 2C:
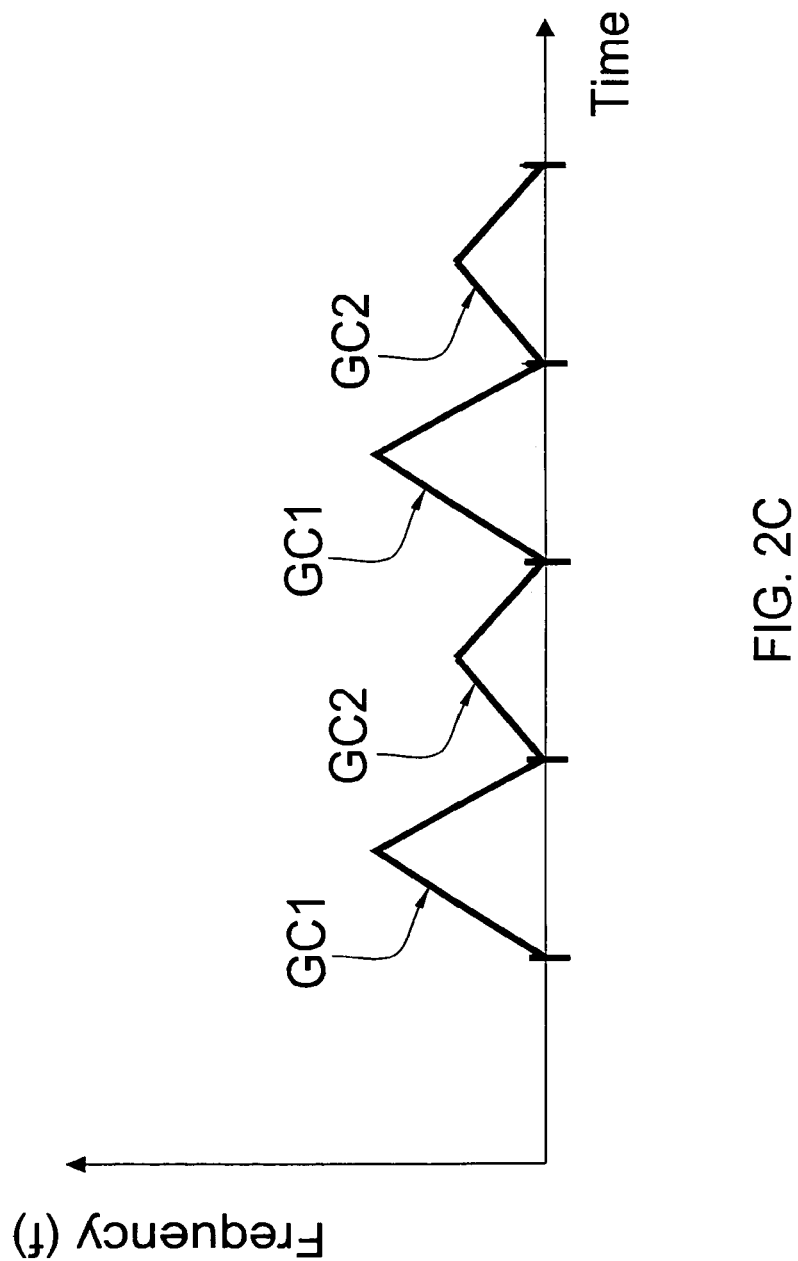
FIG. 2C exemplifies another possible example of affecting an effective optical pathlength of tagged photons scattered from a region of interest.

The control unit 120 processes the measured data MD to determine a relation between data portions corresponding to the different tagged photons, i.e., tagged photons having different effective pathlengths as a result of different characteristics of the acoustic radiation. This relation between the data portions is indicative of a difference in optical attenuation, and is therefore indicative of a tissue property within the illuminated and acoustically irradiated body region. Examples of the acoustics unit operation providing the different characteristics of the acoustic radiation will be described further below with reference to FIGS. 2A-2C.

The data processing includes an appropriate algorithm according to the type of detection used. For example, in the case of a single (large area) detector, a known heterodyne detection technique (e.g., described in Lev A. and B. G. Sfez Optics Letters (2002) 27 (7) 473-475) is used to extract, from the measured data, a data portion indicative of the signal of the tagged photons. When a CCD camera is used and a full speckle image is detected, another known suitable technique for example described by Leveque-Fort et al. in Optics Communication 196 127-131 (2001) can be used to determine the optical signal of photons scattered from the particular volume which is tagged by acoustic waves. Other possible algorithms are described below.

As indicated above, more than one light input port IP as well more than one light output port OP may be provided in the measurement system 100. This is exemplified in FIG. 1B. Here, a measurement system 100 utilizes a pair of light input ports $IP_1$ and $IP_2$ and a pair of light output ports $OP_1$ and $OP_2$. It should be understood that more that two input/output ports can be used. In addition, each port may serve as a dual light input and output port, by using a fiber combiner/splitter that couples light into and out of one optical fiber. The ports may be arranged in a one-dimensional array or a two-dimensional array to improve flexibility of use.

FIG. 1C exemplifies a measurement system 100 having a somewhat different arrangement of input and output ports (or light sources and detectors) within a flexible probe 403. Here, light port $OP_1$ functions as an output port (associated with the illumination assembly), light ports $OP_2$ and $IP_1$ function as respectively output and input ports (associated with the illumination and detection assemblies), and light port $IP_2$ functions as an input port (associated with the detection assembly).

In the examples of FIGS. 1A-1C, the acoustic output port 245 (or transducer arrangement) is located between the light input and output ports. It should, however, be understood that the acoustic port 245 may be placed at any location on the flexible probe 403 (i.e. to the right of light output port OP or the left of light input port IP). Several acoustic output ports, at different locations along the flexible probe 403, may be used being coupled to the same transducer arrangement or to different transducer arrangements. It should also be understood that acoustic port 245 may be located outside the flexible probe 403, being carried by its own support structure configured for attaching to the body part (e.g. skin).

When different acoustic transducer arrangements are used, the transducer arrangements may generate acoustic waves of the same frequency modulation, or each may generate a different frequency modulation. When different frequencies are being generated, the control unit 120 controls the modulation at each transducer arrangement according to the spatial locations of each output port associated with each transducer arrangement, such that light propagating through the same volume as that of the acoustic waves propagation and collected through one or several light input ports is analyzed based on the correct frequency modulation of the corresponding transducer arrangement (as will be described below for one such transducer arrangement). Different transducer arrangements can generate acoustic waves at the same time intervals, or during different time intervals.

As indicated above, a region of interest can be identified by the measurement system 100. This is carried out during the system operation in a calibration mode. Acoustic beams generated by the transducer arrangement or by a plurality of such arrangements, irradiate a plurality of body part regions underlying the probe 403, for example using a phased array for scanning through different regions. Simultaneously, photons are introduced by the illumination assembly to irradiate the body part. Scattered photons are detected by detection assembly. The control unit 120 analyzes tagged and untagged light signals associated with each region, as described above and will be exemplified more specifically further below. The processed signals are then used to determine a parameter of each region. Determined parameters may be compared to reference data to identify the region of interest. For example, a threshold value is defined (prior to applying the actual measurements) for a blood clot or a hemorrhage occupying a predefined volume within a region of interest. The measured parameters are then compared to the threshold value. Region of interest is identified as a region having a determined parameter with a higher value (or lower, or equal with a certain margin) as compared to the threshold. As another example, a different threshold value is defined for an ischemic volume within a region of interest. Determined parameters are then compared to the threshold to determine a region of interest.

The measurement system 100 can be operated to identify a region of interest having a predetermined scattering coefficient. The optimal positioning of the illumination, detection and acoustic assemblies, having a plurality of input and output ports, can be determined by scanning an acoustic beam over different locations inside the body and determining for example the autocorrelation or power spectrum of signals generated by each detection unit in response to photons scattered from different volumes within the body region overlapping with the acoustic beam. As the line-width of the autocorrelation or power spectrum of the tagged signals (frequency modulated), around the frequency of the acoustic radiation, depends on the scattering coefficient of the tagged volume, the control unit can operate to monitor the line width, when the ultrasound beam is used to optimally tag a volume having predetermined scattering properties (e.g. a fluid reservoir such as a blood pool or extravascular fluid).

A region of interest may also be defined by the system operator (e.g., defining region boundaries), and parameters indicative of this region can be recorded by the control unit 120. Control unit 120 determines distances between the region of interest and the acoustic output port 245 and light input and output ports. Thus, the control unit 120 determines an appropriate distance to be provided between the light output port and the light input port, such that photons 250 from the light output port will propagate through region of interest 200 before reaching the input port IP. The control unit 120 can select which output and input ports are used from a plurality of light ports arranged at different spatial locations, such that at least one input port collects photons, emitted from at least one output port, that propagate through the volume of tissue through which acoustic waves 255 propagate. With reference to FIG. 1B or FIG. 1C, the control unit 120 also determines which of the other light input ports (for example light input/output port $OP_2$) collect(s) photons that propagate through surrounding tissues 11 and not tissue region 200.

Additionally, during the calibration mode, the control unit 120 determines a desired frequency bandwidth $\Delta f_1$ that is to be used during the measurements. As indicated above, the control unit 120 may determine the desired frequency bandwidth $\Delta f_1$ to be used during the measurements as that corresponding to a frequency bandwidth optimally filtered by analog or digital electronic filters connected to the light detectors. The bandwidth that these filters optimally transmit is fixed or varied by the control unit 120 during the system operation. The control unit 120 controls a portion of the frequency bandwidth generated by the function generator 122 to correspond to the frequency bandwidth that is optimally transmittable by the electronic filters connected to the light detectors. Alternatively, the bandwidth of the filters is varied by the control unit 120 to correspond to a portion of the frequency bandwidth generated by the function generator.

Following the calibration mode, the control unit 120 operates selected, fixed output and input light ports by modulating (including time gating) the light sources connected only to the chosen output ports, or modulating the output ports themselves, and analyzing the signals generated by the detectors coupled to the chosen input ports.

The control unit 120 controls the time dependent generation of the frequency modulated acoustic waves. The control unit 120 further determines a time period $\Delta t_1$ needed for signal acquisition such that optimal signal-to-noise ratio (SNR) for determining a required parameter (e.g., oxygen saturation) is obtained during the measurements. The time period $\Delta t_1$ is shorter than a time difference between the subject's heart beats, when pulse oximetry is used for data analysis. The control unit 120 also determines the frequency modulation parameters such that the desired frequency bandwidth $\Delta f_1$, (or phase) propagates through the tissue volume 200 during the time period $\Delta t_1$. The onset of time period $\Delta t_1$ is at time $t_1$ equal to about the time for a pulse generated at acoustic port 245 to reach tissue volume 200. Time $t_2$ is determined by $t_2=t_1+\Delta t_1$.

In the examples of FIGS. 1B-1C, the operation of apparatus 100 in a "monitor mode" or actual measurement mode is shown. Considering the example of FIG. 1B, during the monitor mode, the control unit 120 activates the light source(s) associated with the light output port $OP_1$ to emit photons 250 and 251, and actuates the light source(s) associated with the output port $OP_2$ to emit photons 252. The light ports may be associated with different light sources or with one or more common light source. A single light source and preferably two light sources, emitting light of at least two different wavelengths, are connected to the output ports, whereas one light source may be connected to more than one output port. Light sources connected to different output ports, or output ports themselves, may be activated during different time periods and/or with different characteristics (such as different modulation frequency or phase), such that the control unit 120 can distinguish between measured data indicative of detected photons 251 and 252 collected by input ports $IP_1$ and $IP_2$ of the detection assembly.

The control unit 120 also activates the signal generator 122 that, in turn, activates the acoustic transducer arrangement 110 to generate acoustic waves 255 transmitted through the acoustic output port 245. The acoustic wave frequency (or phase) generated by the function generator 122 is modulated by the control unit 120 such that the acoustic waves reaching region of interest 200 illuminated by photons 250 will have a predetermined frequency bandwidth $\Delta f_1$. If the bandwidth $\Delta f_1$ is fixed, then the control unit 120 determines the frequency modulation of the function generator controlling the generation of acoustic waves 255, such that acoustic waves 255 modulated at a frequency within $\Delta f_1$ reach tissue volume 200 at time $t_1$. In addition, acoustic waves with a frequency within $\Delta f_1$ substantially do not propagate through other tissues during the time period $\Delta t_1$ following time $t_1$. Accordingly, the control unit operates the detection assembly 102A such that the light detectors associated with the input ports $IP_1$ and $IP_2$ start collection of photons at time $t_1$ and end the collection process during time $t_2$. Alternatively or additionally, the control unit 120 controls the activation of light sources associated with the output ports $OP_1$ and/or $OP_2$ at time $t_1$ and ends the activation at time $t_2$. During the time period $\Delta t_1$, input port $IP_2$ and/or input port $IP_1$ collect photons 250 propagating through the same tissues through which acoustic waves 255 propagate (a time delay in photon propagation through the tissue, which is on the order of a nanosecond, is neglected). Photons 251 essentially do not propagate through same tissue region through which acoustic waves having a frequency within $\Delta f_1$ propagate during time period $\Delta t_1$.

Figure 1E:
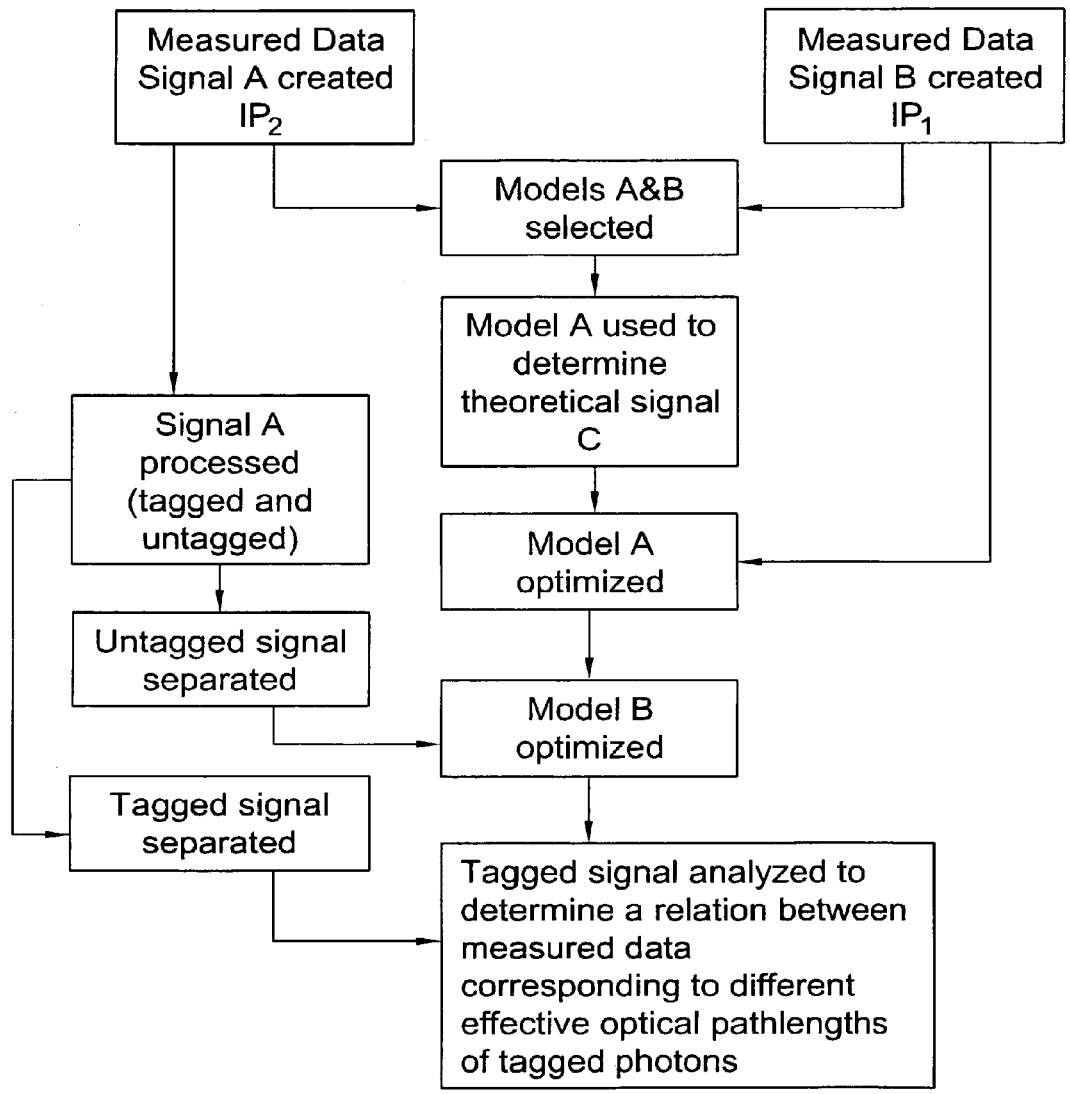
FIG. 1E is a flow diagram of an example of a measurement technique of the present invention.

Reference is made to FIG. 1E more specifically describing an example of the system operation and data processing procedure considering the system configuration of FIG. 1B or 1C. The input port $IP_2$ receives photons 250 including tagged and untagged photons scattered by the surrounding tissues 11 and tagged photons scattered by the tissue volume of the region of interest 200, while the input port $IP_1$ receives primarily only untagged photons 251 scattered by surrounding tissues 11. A signal that is generated by the detection assembly 102A in response to photons 250 collected at input port $IP_2$ is referred to as "signal A". A signal generated by the detection assembly 102A in response to photons 251 collected at input port $IP_1$ is referred to as "signal B".

According to this example, two models are selected to describe the propagation of light in a multi layer tissue body. Such models are described for example by Keinle et al. in Physics in Medicine and Biology 44: 2689-2702 (1999). One model (Model A) includes the parameters representing some of the tissues through which photons 251 propagate from the output port $OP_1$ through a medium until they reach the input port $IP_1$, and the other model (Model B) includes the parameters representing some of the tissues in the medium through which tagged photons 250 propagate until they reach input port $IP_2$. The models include known parameters, such as the molar absorption and scattering coefficients of blood cells, and of oxygenated hemoglobin and deoxygenated hemoglobin at each of the wavelengths of illuminating photons. In addition, the models may include the thickness of the layers, presence and volume of fluid in the light path and other parameters that are measured during the operation of apparatus 100. Some tissue parameters in the model may be averaged or other manipulations of the known or measured parameters of the real tissues in models A and B may be carried out.

Given a certain amplitude of illuminating light, and the known separation between the light output port $OP_1$ and the input port $IP_1$, model A is used to calculate the expected time dependent photon flux, or light intensity at the input port of the detection assembly 102A. The expected time dependent photon flux or light intensity is used to calculate the expected signal (termed "signal C") that can be generated by the detection assembly 102A in response to such a photon flux. Signal C actually presents theoretical data for untagged photons at the location of detection assembly 102A, while signal B presents real measured data for untagged photons collected by the detection assembly 102A.

The parameters of model A are adjusted (optimized) such that signal C is made equal to or closely resembles signal B (best fitting). Signal processing techniques based on optimization algorithms, such as neural network, can be used to optimally determine the parameters of model A. The parameters are used to calculate the optical properties of some of the tissues through which photons 251 propagate.

It may generally be assumed that the optical properties of tissues outside the region of interest (i.e., within regions 11) through which both photons 250 and 251 propagate are similar. Alternatively, it may be assumed that by determining the parameters and optical properties of the tissues through which photons 251 propagate, one can deduce, within a reasonable error, the optical properties of corresponding tissues through which photons 250 propagate. The parameters calibrated by signal B and the optical properties of the tissues through which photons 251 propagate are then used to calibrate (optimize) model B that describes the propagation of photons 250 through surrounding tissues.

The time dependent amplitude of signal A at all wavelengths of photons 250 is processed by the control unit 120 using techniques known in the art, such as digital Fourier transformations and analog or digital filtering, to extract, from the entire signal A, a signal portion corresponding to the tagged photons 155. This signal portion is termed "tagged signal A". Tagged signal A is that modulated at the acoustic frequency generated by the transducer arrangement 110. The amplitude of the power spectra of the tagged signal A at the acoustic frequency (or related to the acoustic frequency), the modulation width of its power spectra or other features of tagged signal A, such as its phase, are termed together as "processed tagged signal A" This processed tagged signal A is actually indicative of both the surrounding tissues response and the response of the region of interest tagged by the acoustic radiation. In addition, the signal A contains information which is not modulated at the acoustic frequency, termed "untagged signal A".

According to this specific embodiment, untagged signal A may also be used in the data processing and analyzing procedure, for example to determine some of unknown parameters of model B and further optimize this model.

As indicated above, the control unit 120 processes the measured data (using an appropriate algorithm according to the type of detection used) to extract the measured data portion indicative of tagged photons, and process this data portion to identify a light response of region 200 (photons scattered at region 200) by determining a relation between the tagged signals corresponding to different effective pathlengths of the tagged photons.

Using the above-indicated, or other suitable techniques, it is possible to determine the effective attenuation of photons as they propagate through the region of interest. To this end, acoustic radiation may be applied such that acoustic waves 255 propagate through different depths of tissues (e.g., by displacing the transducer arrangement with respect to the body or by using a phase array transducer). Accordingly, the absorption coefficient and the reduced scattering coefficient can be isolated for the two wavelengths chosen for illumination. For example, using a similar equation to equation 4 of the above-indicated Lev et al. reference:

$$x = \frac{\gamma_6^O - \frac{\mu_{eff,6}}{\mu_{eff,8}}\gamma_8^O}{\left[(\gamma_8^H - \gamma_8^O) - \frac{\mu_{eff,6}}{\mu_{eff,8}}(\gamma_6^H - \gamma_6^O)\right]}$$

it is possible to determine the oxygen saturation level of the region of interest. Here, x is the fraction of deoxyhemoglobin, $\gamma$ are the molar extinction coefficients of oxyhemoglobin (O) and deoxyhemoglobin (H) at both wavelengths (in the referenced paper, 6 stands for 690 nm and 8 for 820 nm) and $\mu_{eff,6}$ and $\mu_{eff,8}$ are the measured attenuation coefficients at 690 and 820 nm, respectively.

The acoustic transducer arrangement 110 (or its output port) is kept at a specific location, which is optimal for propagating acoustic waves through the same volume tissue from which scattered photons are detected by the detection assembly. The beam size of transducer 110 is such that the cross section volume between photons and acoustic waves is determined by control unit 120 to achieve a high signal to noise ratio (SNR).

The control unit 120 analyzes both back and forward scattered tagged photons to determine the optical attenuation of light propagating through the region of interest. Consequently, the control unit 120 needs not perform high resolution imaging of the region of interest, but rather analyzes the collected photons scattered within a significant volume of the targeted tissues.

The control unit 120 processes that portion of the measured data, which is associated with tagged photons 250 scattered from the region of interest, to determine the desired parameter of the region of interest—oxygen saturation in the present example. Two modalities can optionally be used to determine the oxygen saturation level, one being based on measuring the average oxygen saturation level (known as oximetry) and the other being based on measuring the oxygen saturation level correlated with changes in the blood volume during the cardiac cycle (known as pulse oximetry).

Oxygen saturation S is a ratio between the concentration of oxygenated hemoglobin [HbO] and the total concentration of hemoglobin [HbT] in blood:

$$S = [HbO]/[HbT]\,(*100\%) \quad [1]$$

$$[HbT] = [HbO] + [Hb] \quad [2]$$

wherein [Hb] is the concentration of deoxygenated hemoglobin.

The saturation S can be extracted from the attenuation coefficient measured for at least two wavelengths $\lambda_1$ and $\lambda_2$, where the molar absorption and scattering coefficients for Hb and HbO at each wavelength are known in the literature. It should be noted that more than two wavelengths can be used, to improve sensitivity of the measurement.

As the arteries expand, a blood volume [HbT] is increased by [ΔHbT], therefore absorption changes periodically. The optical attenuation at $\lambda_1$ and $\lambda_2$ is measured at predetermined points (for example, the maxima and minima of a power spectrum of the tagged signal or the processed tagged signal, as defined below) generated by the detection assembly 102A during a cardiac cycle. The saturation S can be calculated from differences in attenuation of light ($\Delta OD^\lambda$) at each wavelength between maxima and minima.

$$\Delta OD^\lambda = (\gamma_{HbO}^\lambda \cdot [\Delta HbO] + \gamma_{Hb}^\lambda \cdot [\Delta Hb]) L^\lambda = (\gamma_{HbO}^\lambda S + \gamma_{Hb}^\lambda (1-S))[\Delta HbT] L^\lambda \quad [3]$$

wherein $\gamma_{HbO}^\lambda, \gamma_{Hb}^\lambda$ are the molar attenuation coefficient of oxygenated and deoxygenated hemoglobin respectively, at wavelength $\lambda$ ($\lambda = \lambda_1, \lambda_2$), $L^\lambda$ is the effective optical pathlength from the illumination assembly (its light output port) to the detection assembly (its light input port), which accounts for tissue scattering. The factor $L^\lambda$ can be estimated by solving the photon diffusion equation for the appropriate measurement geometry (for example as disclosed in A. Zourabian et al. "*Trans-abdominal monitoring of fetal arterial blood oxygenation using pulse oximetry*" Journal of Biomedical Optics 5(4), 391-405 (2000)).

Defining the ratio R between $\Delta OD^\lambda$ at each wavelength $\lambda_1$ and $\lambda_2$, assuming $L^{\lambda_1}$ substantially equals $L^{\lambda_2}$, we get:

$$R = \frac{\Delta OD^{\lambda_1}}{\Delta OD^{\lambda_2}} = \frac{[\gamma_{HbO}^{\lambda_1} S + \gamma_{Hb}^{\lambda_1}(1-S)]}{[\gamma_{HbO}^{\lambda_2} S + \gamma_{Hb}^{\lambda_2}(1-S)]} \quad [4]$$

where saturation S is extracted from equation [4] when $\Delta OD^{\lambda_1}$ and $\Delta OD^{\lambda_2}$ are measured and the molar attenuation coefficients are known. In cases $L^{\lambda_1}$ does not substantially equal $L^{\lambda_2}$, it can be determined empirically (see above reference A. Zouràbian et al), or wavelength selection is determined such that the two parameters are substantially equal.

When monitoring a tissue region, or when there is negligible pulsation, $\Delta OD^\lambda$ is determined as the difference in a parameter of the optical signal between two different measurement conditions as defined below.

According to an embodiment of the present invention, the control unit analyzes signals generated by the detection assembly in response to each wavelength $\lambda_1, \lambda_2$ generated by the illumination assembly. The tagged signals corresponding to collected tagged photons are selected by the detection assembly using the principles of interference with a local oscillator, or by the control unit 120 using frequency analysis and/or speckle imaging. The time dependent amplitude and/or phase of the tagged signals for each wavelength $\lambda_1, \lambda_2$ is stored in the memory of the control unit 120, over a specified period of time determined to optimize the output signal, e.g. increase the SNR. To determine the oxygen saturation level of the region of interest, the control unit 120 determines the time dependent changes in attenuation of tagged signals at each wavelength.

Considering the determination of oxygen saturation of a region of interest 200 based on oximetry, the time averaged signals generated by the detection assembly in response to the tagged photons of at least two illuminating wavelengths collected by the light input port, are used to determine the oxygen saturation level. Time averaging can be performed over longer time scales than the duration of a heart cycle.

When considering pulse oximetry used for determining oxygen saturation level, the temporal changes (due to the cardiac cycle) in the blood volume are monitored by the control unit 120 by monitoring the low-frequency changes (0.5-2.5 Hz) in the signals generated by the detection assembly in response to the tagged photons of at least two illuminating wavelengths reaching the light input port of the detection assembly. Since the ultrasound frequency is orders of magnitude higher than the heart rate, it is possible to average the signals responsive to tagged photons over a fraction of the heart cycle to improve the SNR of the measurement. Using methods of pulse oximetry, both the oxygen saturation and the pulse rate are determined simultaneously.

The control unit 120 displays the determined oxygen saturation level, along with heart rate, as a function of time. The heart rate is determined by low-frequency analysis of the tagged signals. The control unit 120 optionally alerts using a suitable indication utility (e.g. sound and/or light signal), when oxygen saturation level drops below a certain threshold (for example 50% or 70%)

In an embodiment of the present invention, the optical unit is configured as a pulse oximeter, namely includes illumination assembly 101A configured to generate light of at least two different wavelengths and light detection assembly 102A; and is used in combination with acoustic transducer arrangement 110 to significantly improve the pulse oximetry measurements. The measurement system may be configured to operate in a transmission mode (light transmission based detection), such as the conventional pulse oximeter placed on a finger or earlobe. In this case, support structure 403 is located such that illumination assembly 101A is co-linear with detection assembly 102A: illumination assembly 101A is placed at one side of the tissue and detection assembly 102A is placed at the opposite side of the tissue, therefore ballistic and scattered light emitted from illumination assembly 101A are detected by detection assembly 102A. Transducer arrangement 110 is placed such that acoustic waves overlap with an illuminated region in the region of interest from which scattered light reaches detection assembly 102A, which is preferably the region encompassing a blood vessel (e.g. an artery) or a collection of arterial vessels. In other applications, requiring reflection based detection from a region of interest ("reflection mode"), measurement system 100 is located as described above, where the region of interest preferably encompasses a blood vessel (e.g. an artery) or a collection of arterial vessels. Such an arrangement is superior to conventional pulse oximeter as it is not affected by incoherent ambient light, and more important is less affected by motion of the tissue relative to illumination and detection assemblies, as long as the region of interest is kept illuminated and the acoustic waves propagate through it.

It should be understood that using the acoustic tagging of light in the pulse oximetry based measurements significantly improves the measurements, since the measured tagged light signal is practically insensitive to movements of the region of interest under measurements, which is the common problem of the typical pure pulse oximetry measurements.

As indicated above, the at least two different effective pathlengths of scattered tagged photons are achieved by appropriately operating the acoustic transducer arrangement with at least two different measurement conditions (corresponding to two different values of a characteristic of acoustic radiation). Considering the oxygen saturation measurements, this provides for determining the oxygen saturation level of a region of interest without depending on the pulsating blood volume. This is particularly important for measuring regional tissue oxygenation, or venous oxygenation or when pulsation is negligible. Control unit 120 controls the measurement conditions by controlling at least one activation parameter of transducer arrangement 110, such that transducer arrangement 110 emits at least two different acoustic signals having two different activation parameters during the illumination of the region of interest by a single wavelength or by each one of at least two different wavelengths of light (or vice versa). The at least one activation parameter includes but is not limited to the following: duration of acoustic pulse or burst of waves, amplitude, frequency, number of elements activated in a phased array, focal length of the transducer arrangement, focal dimensions (e.g. acoustic beam waist at focal distance) of the transducer arrangement or gradient of chirp in frequency of the acoustic waves.

The measurement conditions are determined such that the tagged volume in each measurement is within the region of interest, and that the average optical and acoustic characteristics of the tagged volumes are about the same during and in between the two measurements. It is clear that two or more measurements conditions can be changed between measurements. For example, two sets of measurements are taken with two different pulse durations, where the first set has one acoustic wave amplitude and the second set is at a second acoustic wave amplitude. All measurements are then used to determine a parameter of the region of interest.

Let us consider a signal generated by detection assembly 102A indicative of the light response of the tagged volume:

$$I_t(t) = C|E_U \exp[i(\omega_L t + \phi_U)] + E_T \exp[i((\omega_L + \Omega_{US})t + \phi_T)]|^2 \quad [5]$$

wherein C is a proportionality constant depending on the efficiency of the detection assembly and the area of the light input port IP, $E_U$ is the absolute amplitude of the untagged electromagnetic field, $E_T$ is the absolute amplitude of the tagged electromagnetic field, $\omega_L$, is the light frequency, $\phi_U$ and $\phi_T$ are the phases of the untagged and tagged electromagnetic fields respectively, and $\Omega_{US}$ is the acoustic frequency.

As the tagging efficiency (the number of tagged photons relative to the number of untagged photons scattered by scattering centers inside the tagged volume) is small (i.e. $I_U = |E_U|^2 >> |E_T|^2 = I_T$), the detected signal $I_t(t)$ can be written as:

$$I_t(t) = C(|E_U|^2 + |E_T|^2 + 2E_U E_T \cos(\Omega_{US} t + (\phi_U - \phi_T))) \cong I_U + I_{UT} \quad [6]$$

The first term is a DC component, whereas the second term is modulated at the acoustic frequency. The amplitude of the second component, sampled at the acoustic frequency, divided by the DC component gives:

$$\frac{I_{UT}(@\Omega_{US})}{I_U} = \frac{2E_T}{E_U} = 2\sqrt{\frac{I_T}{I_U}} \quad [7]$$

The optical attenuation $OD^\lambda$ of light at a specific wavelength $\lambda$ is defined by the modified Beer-Lambert law as:

$$OD^\lambda = \frac{-1}{2.3} \ln\left[\frac{I^\lambda}{I_0^\lambda}\right] = \alpha^\lambda L^\lambda + G \quad [8]$$

wherein $I^\lambda$ is the output intensity of light, $I_0^\lambda$ is the input intensity of light, $\alpha^\lambda$ is the absorption at wavelength $\lambda$ (that depends on the concentration of the chromophores), $L^\lambda$ is the effective optical pathlength which accounts for scattering and G is a geometrical measurement factor.

For the tagged and untagged signals, using equation 8 we can write:

$$I_T = C_1 I_0 \exp[-\alpha^\lambda L_T^\lambda - G] \equiv C_1 I_0 \kappa_T^\lambda \exp[-G] \quad [9a]$$

$$I_U = C_2 I_0 \exp[-\alpha^\lambda L_U^\lambda - G] \equiv C_2 I_0 \kappa_U^\lambda \exp[-G] \quad [9b]$$

wherein $C_1$ and $C_2$ are constants, and $L^\lambda_T$ and $L^\lambda_u$ are the effective optical pathlengths of the tagged and untagged photons respectively. Assuming that changes in the effective pathlength of tagged photons ($\Delta L_T$) within the tagged volume depend primarily on the changes in the characteristics of the acoustic radiation and are essentially independent on the wavelength of light:

$$\frac{\Delta \kappa_T^\lambda}{\kappa_T^\lambda} = -[\Delta \alpha^\lambda L_T^\lambda + \alpha^\lambda \Delta L_T] \quad [10a]$$

$$\frac{\Delta \kappa_U^\lambda}{\kappa_U^\lambda} = -\Delta \alpha^\lambda L_U^\lambda \quad [10b]$$

In equations 10a and 10b it is assumed that the effective optical pathlength in the tagged volume is changed, whereas the effective optical pathlength in the untagged volume is unchanged, and that the tagged volume is much smaller than the untagged volume, and thus a change in the effective optical tagged pathlength has negligible effect on the untagged signal. As $\Delta \alpha^\lambda$ represents changes in the concentration of the chromophores in the media, it can be neglected during the measurement where there is negligible changes in their concentrations (i.e. when there is no pulsation in case of blood related measurement, or when the changes in the chromophores concentration occur over a much longer time scale then is accepted by the measurement conditions).

Thus, by introducing a change in the at least one characteristic of the acoustic radiation (e.g., resulting in a change in the effective optical pathlength within the tagged volume) in between two consecutive measurements, the absorption coefficient of the chromophores within the tagged volume can be determined.

The tagged signal, extracted from the measured signal during the first measurement is marked $I_{T1}$, and the tagged signal during the second measurement is marked $I_{T2}$. Thus:

$$\frac{I_{T1} - I_{T2}}{I_{T1}} = \frac{(\kappa^\lambda_{T1} - \kappa^\lambda_{T2})}{\kappa^\lambda_{T1}} = \frac{\Delta\kappa^\lambda_{T1}}{\kappa^\lambda_{T1}} = \alpha^\lambda \Delta L_T \quad [11]$$

For the case of oxygenated and deoxygenated hemoglobin $\alpha^\lambda = (\gamma_{HbO}{}^\lambda[HbO] + \gamma_{Hb}{}^\lambda[Hb]) = (\gamma_{HbO}{}^\lambda S + \gamma_{Hb}{}^\lambda(1-S))[HbT]$ for two different wavelengths $\lambda_1$ and $\lambda_2$ we get:

$$R = \frac{\alpha^{\lambda_1} \Delta L_T}{\alpha^{\lambda_2} \Delta L_T} = \frac{(\gamma^{\lambda_1}_{HbO} S + \gamma^{\lambda_1}_{Hb}(1-S))}{(\gamma^{\lambda_2}_{HbO} S + \gamma^{\lambda_2}_{Hb}(1-S))} \quad [12]$$

Hence, Eq. 12 is equivalent to Eq. 4. Therefore inducing small changes ($\Delta L_T \ll L^\lambda_T$) in the effective optical pathlength of the tagged photons in order to determine the oxygen saturation level within the tagged volume is equivalent to chromophore concentration change.

The following are non limiting examples of introducing a change in at least one characteristic of acoustic radiation.

The control unit operates to control generation of the acoustic radiation to create a tagged volume $V_T$, such that small changes in $V_T$ correspond to small changes in the effective optical pathlength of tagged photons. According to the present invention, the different tagged volumes substantially overlap in space.

Figure 3:
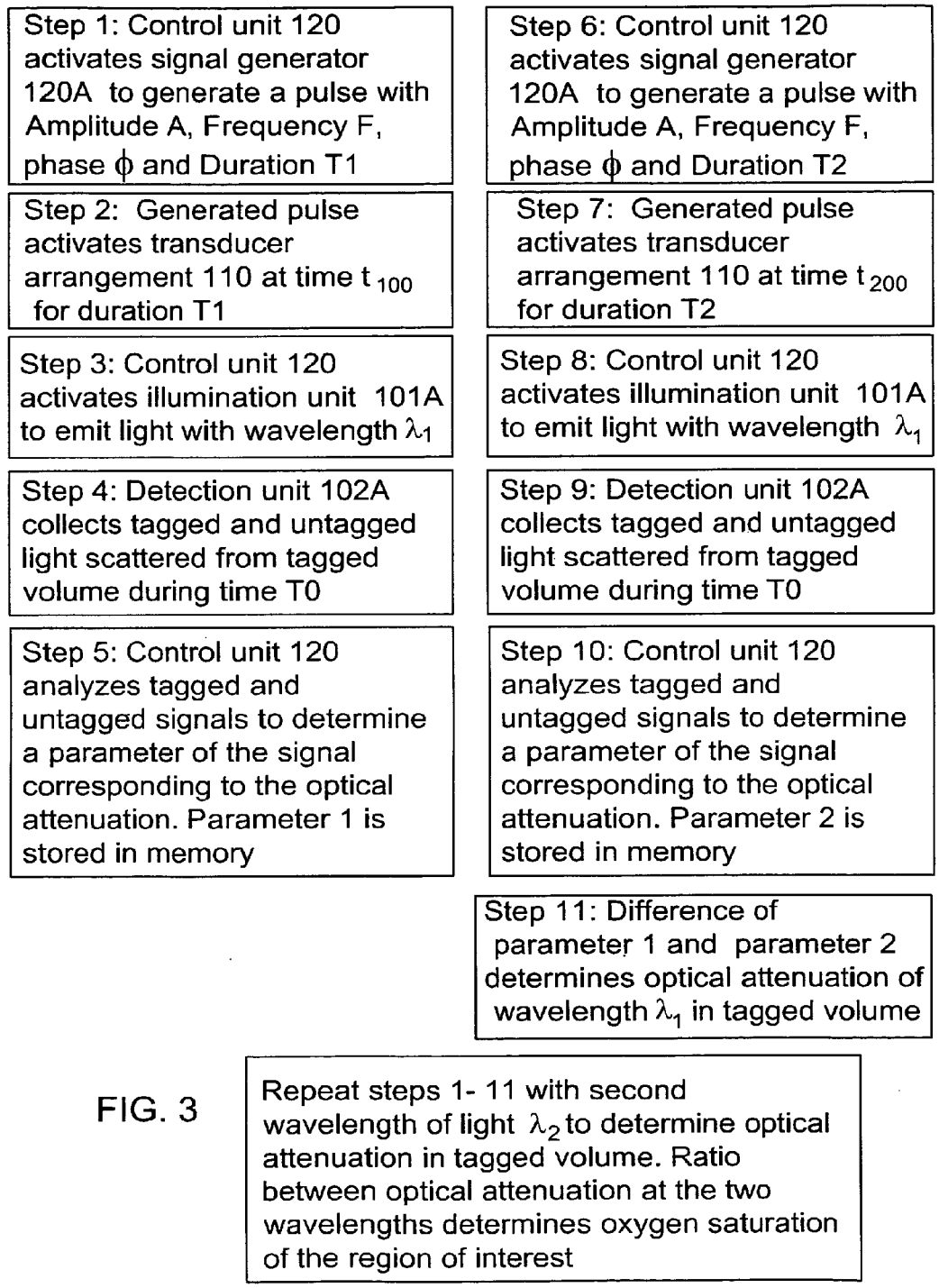
FIG. 3 is a flow diagram of an example of a method of the invention utilizing the measurement scheme of FIGS. 2A and 2B.

For example, the control unit operates to control the activation of a signal generator (122 in FIG. 1A), such that the signal generator transmits two bursts (or pulses) with the same or different repetition rate for each burst. This is exemplified in FIGS. 2A and 2B; an example of a measurement method is shown as a flow diagram in FIG. 3. For clarity, only relevant elements of the measurement system 100 overlaying a region of interest 200 are shown in FIG. 2A-2B.

A control unit (not shown) activates a signal generator to produce an acoustic burst with a specific amplitude A, frequency F and phase $\phi$. The generated pulse activates the transducer arrangement at time $t_{100}$ for duration $T_1$. This burst, termed "$T_1$ burst", propagates through surrounding tissues in the body part and reaches a region of interest 200 at time $t_0$. The control unit activates an illumination assembly 101A to emit light of at least one wavelength $\lambda_1$. The control unit activates the collection of signals from a detection assembly 102A at time $t_0$ following $t_{100}$. Detection assembly 102A collects tagged and untagged light coming from the body part during time $T_0$. During time $T_0$ (following time $t_0$), acoustic waves have propagated a distance D from acoustic output port 245. The spatial length, $d_1$, of burst $T_1$ is equal to the product $T_1 \cdot C_s$ where $C_s$ is the speed of acoustic wave propagation (e.g., speed of sound) in the region of interest. A volume 266 that is been tagged by burst $T_1$ at any point in time is equal to $d_1$ times a cross section A' of the acoustic beam. For example, a planar acoustic wave with a uniform cross section A' may be assumed, thus volume 266 is equal to $V_1 = T_1 \cdot C_s \cdot A'$. The control unit operates to analyze the measured data (detected tagged and untagged signals) to determine a parameter of the signal corresponding to the optical attenuation (e.g. the amplitude of the power spectrum of the detected signal at the acoustic wave frequency). The determined parameter is stored in the memory utility The control unit activates the signal generator to generate a second burst having the same amplitude A, frequency F and phase $\Phi$. The generated pulse activates the transducer arrangement at time $t_{200}$ for a duration $T_2$ ($T_2$ being different from $T_1$). This burst, termed "$T_2$ burst", propagates through the surrounding tissues in the body part and reaches a region of interest 200 at time $t_0$.

It is clear that a plurality of $T_1$ bursts can be emitted sequentially prior to emission of a plurality of $T_2$ bursts, as long as the optical and acoustical properties of the tissues do not change during the two series of pulses. A series of signals each corresponding to a series of $T_1$ and $T_2$ bursts will be analyzed as a long burst. In such cases it is preferred that the burst of acoustic waves are phased locked in order to improve SNR. The signals are concatenated, as to form a long time dependent signal, and then analyzed as being a result of one long burst.

Burst $T_2$ propagates the same distance D during time $T_0$ following time $t_0$. Burst $T_2$ occupies a volume 267 equal to: $V_2 = T_2 \cdot C_s \cdot A'$. For a planar acoustic wave, the difference in the tagged volume is: $\Delta V_T = V_1 - V_2 = (T_1 - T_2) \cdot C_s \cdot A'$. The control unit also activates illumination assembly 101A to emit light with at least one wavelength $\lambda_1$. The control unit activates the collection of signals from a detection assembly 102A at time $t_0$ following $t_{200}$.

The control unit activates the detection assembly 102A to collect tagged and untagged light signals for the duration $T_0$ being preferably shorter than the shortest duration of the bursts (i.e. the smallest of $T_1$ or $T_2$). As the tagged volume is varied, the number of tagged photons reaching the detector input port will vary. The control unit analyzes the respective measured data to determine the same parameter of the signal corresponding to the optical attenuation (as for burst $T_1$), and stores this parameter in the memory utility. Thus, for each burst $T_1$ and $T_2$, the control unit records the tagged and untagged signals, and stores them in the memory.

The above technique is repeated for each wavelength $\lambda_1$, $\lambda_2$, and for each wavelength the difference in the tagged signal ($I_{T1} - I_{T2}$) is calculated from the difference in the tagged signal parameter (for example, amplitude of tagged signal power spectrum at the acoustic frequency, being normalized or not by the untagged signal relevant parameter) between bursts $T_1$ and $T_2$, and equation 12 is used to determine the oxygen saturation level.

As another example, the different operating conditions of acoustic radiation generation (providing different effective optical pathlengths) are achieved by controlling the waist of the acoustic beam. The control unit determines the waist of the acoustic beam by controlling a beam aperture or a number of acoustic elements activated in the transducer arrangement 110, forming a phase array. The focal distance of the array is unchanged in between bursts, and only the beam dimensions are varied in between the two bursts (i.e. one burst having beam waist $BW_1$ and the other $BW_2$). Similarly to the above-described example of different pulse durations, here the tagged signal is determined for each waist $BW_1$ and $BW_2$ and the relative difference in parameters of the tagged signal is determined for each burst. The process is repeated for each of the at least two illuminating wavelengths, and the parameter of the tissue is determined.

The tagging efficiency, defined as the number of tagged photons relative to the number of untagged photons scattered by scattering centers inside the tagged volume, is known to depend on the frequency of the acoustic beam, the speed of the acoustic wave in the tissue, and on the amplitude of the acoustic radiation in the tagged volume. Therefore changes of the frequency of the acoustic radiation, the intensity (or power) of the acoustic beam, and the speed of acoustic wave (sound) in the tissue affect changes in the effective optical pathlength of the tagged photons.

Assuming a constant tagging efficiency in between the two measurement conditions as explained above, the normalized amplitude at the acoustic frequency corresponds to the optical attenuation of the media. Assuming that the average optical and acoustic properties of the illuminated media are about the same in between the two measurements, the difference or ratio between the optical attenuation at the two measurement conditions corresponds to the optical properties of the region of interest The effective optical pathlength can also be varied in between measurements by varying the tagging efficiency.

As an example, the amplitude of the acoustic waves can be varied between two or more acoustic bursts. For example, the transducer arrangement generates one burst with amplitude $A_1$ and the other with amplitude $A_2$ different from $A_1$. As the tagging efficiency depends on the amplitude of the acoustic waves, measured data is indicative of two different tagged signals generated by the detection assembly in response to collected photons at each burst of acoustic waves with amplitude $A_1$ and $A_2$. The difference or the relative difference between the two signals corresponds to the effect of the acoustic waves' amplitude on the tagged signals and can therefore be determined by this measurement.

As yet another example, the frequency of the acoustic waves is varied between two bursts (or two series of bursts) one having a frequency $F_1$ and the other a second frequency $F_2$. In case of a focused acoustic beam, assuming no chromatic aberrations of an acoustic lens assembly used in the transducer arrangement, the dimensions of the focal volume (i.e. the beam diameter and length of the focal zone) are known to depend on the frequency of the acoustic radiation. Consequently, different frequencies will be focused into different volumes, and the volume of the tagged region will be different for each frequency. In addition, the tagging efficiency depends on the frequency of the acoustic waves. Both effects result in a different effective optical pathlength. The control unit activates the signal generator to emit bursts having the same amplitude, phase and duration, but two different frequencies $F_1$ and $F_2$. This measurement scheme is repeated for each wavelength $\lambda_1$ and $\lambda_2$ of illuminating light, and for each wavelength the difference in attenuation is calculated from the difference in the tagged signal parameter (for example, amplitude of the tagged signal power spectrum at the acoustic frequency) between bursts having frequency $F_1$ and $F_2$, and Eq 12 is used to determine the oxygen saturation level.

As yet another example, the acoustic frequency of each burst may be modulated (for example having a chirp) such that the signal generator generates continuously chirped signals (thus a "burst" refers to a single cycle of chirping). The control unit determines frequency range $\Delta f_1$ as described above, to propagate through tissue volume 200 during time $\Delta t_1$ following time $t_0$. As exemplified in FIG. 2C, during one cycle of chirped cycles (cycle 1), the gradient of the chirping $(\partial f/\partial t)$ is equal to $GC_1$ and during a second cycle of chirped cycles, the gradient of the chirping $(\partial f/\partial t)$ is equal to $GC_2$.

The control unit activates an illumination assembly 101A to emit light of at least one wavelength $\lambda_1$. The control unit activates the collection of signals from a detection assembly 102A at time $t_0$. The process is repeated for the different optical wavelengths for each set $GC_1$ and $GC_2$, and the processed signals (e.g. power spectrum of tagged signal) are stored in memory. Again, a parameter of the tagged and untagged signal is determined for each cycle $GC_1$ and $GC_2$, and stored in memory. A difference between the normalized tagged signals is determined for each wavelength as the difference in that parameter for each wavelength, for the two cycles.

As the tagging efficiency depends on the acoustic properties, but the overall tagged signal depends on both the optical and acoustic properties of the tagged volume, the different measurement conditions can be used to decouple the effects of the tagging efficiency on the overall signal. This is achieved, for example, by performing four different measurements, one pair indicative of two different pulse durations with one amplitude, and the second having the same two pulse durations at the other amplitude of acoustic waves. For each pair of measurements $\Delta\alpha^\lambda$ is determined as above, and then the difference between the determined values (if exists) accounts for changes in the tagging efficiency. Once this dependence is established, it can be used to determine the effect of the acoustic parameters on the measured signals. Alternatively, three different optical wavelengths can be used to determine a relative measurement condition, where the acoustic properties are the same in between the measurements. The measurement is repeated for each of the three wavelengths, at two different measurement conditions, and the acoustic properties are decoupled from the determined signals.

The following is an example of using the system of the present invention for imaging a tissue region in a body, namely mapping the optical attenuation (i.e., determining the optical attenuation parameter at each location). Control unit 120 operates ultrasound transducer arrangement 110 to scan different tissue volumes. The intensity of each pixel or voxel in the image is determined as follows:

Step 1: The signal generator 122 is activated to transmit a signal to transducer arrangement 110 to generate one acoustic burst $T_1$.

Step 2: The illumination and detection assemblies are activated at a certain time delay $t_d$, such that acoustic burst $T_1$ propagated a distance $D_d$ from acoustic port 245 which is determined as $D_d = C_s \cdot t_d$. In case transducer arrangement 110 is a phased array, then control unit 120 also determines the angle $\Theta_d$ between the acoustic port 245 and the acoustic beam propagation direction. Control unit 120 processes and analyzes signals (measured data) generated by detection assembly 102A during time $T_0$ (as defined above), and stores parameters of processed signals in memory.

Step 3: Step 1 and Step 2 are repeated using the same time delay $t_d$ parameter (and angle $\Theta_d$ parameter, where applicable) while ultrasound burst $T_2$ is generated by acoustic arrangement 110.

Step 4: Control unit 120 then analyzes the stored parameters of light-indicative signals generated during bursts $T_1$ and $T_2$ to determine a property of the tissue volume being tagged by acoustic radiation at distance $D_d$ (and angle $\Theta_d$, where applicable) from the acoustic port. A certain value is then assigned to the so-determined property (for example degree of oxygen saturation of that volume).

Step 5: The assigned value is displayed as a two or three dimensional image on a display, where the location of the pixel/voxel corresponds to the distance $D_d$, and angle $\Theta_d$ from acoustic port 245 (the location of acoustic port 245 may serve as the "zero position" on the display where all the distances are calculated relative to that zero position).

Steps 1-5 are repeated for different delays $t_d$ (and different angles $\Theta_d$) and a full image is displayed, where the value of each pixel is translated to a color scale, a grey level scale or a numerical scale representing the value of a parameter (such as hemoglobin concentration or oxygen saturation).

The technique of the present invention can be used to determine the concentration of blood or the volume of blood or other chromophores within the region of interest. For determining the blood volume, a single wavelength corresponding to the isosbestic point of oxygenated and deoxygenated hemoglobin can be used, but preferably two or three wavelength of light are used, whereas at least one corresponds to the isosbestic point. For determining blood volume or concentration within the tagged volume, two characteristically different bursts of acoustic waves are generated by transducer arrangement (as described above for oxygen saturation). For each burst, the tagged signals and the untagged signals are detected and corresponding measured data is collected by the control unit during a time period corresponding to the propagation of the acoustic waves inside the region of interest. The signals are recorded and stored in memory for each wavelength of light. For the isosbestic point, $\gamma_{HbO} = \gamma_{Hb} = \gamma_{HbT}$, and from equation 12 above, we get:

$$\Delta OD^{\lambda} = \gamma_{HbT}^{\lambda [HbT] \Delta L}{}_T \quad [13]$$

The total volume of blood within the tagged volume can be calculated if $\Delta L_T$ is known. Preferably, two or more wavelengths are used to determine the concentration of hemoglobin in the region of interest, as explained above.

It is known that the optical properties of a blood clot or an internal hemorrhage can be determined by near infrared spectroscopy [B. Chance et al "*Optical investigations of physiology: a study of intrinsic and extrinsic biomedical contrast*" Phil. Trans. R. Soc. Lond. B (1997) 352, pp. 707-716]. Therefore, by monitoring the changes in the tagged signals from a region of interest within a hematoma or a hemorrhage, the control unit can operate to determine a hemorrhagic event, and possibly the time-span of a hemorrhage, or changes in the blood volume of an existing hemorrhage.

According to another embodiment of the invention, the region of interest is a blood vessel or blood-filled cavity such as a ventricle, sinus or bulb. Oxygenation of blood inside the region of interest is monitored using a measurement system of the present invention. For example, venous oxygen saturation is measured in the Jugular vein bulb using a modified probe. The Jugular vein bulb is located at the base of the skull, about 2-3 cm behind the ear canal. It is therefore advantageous to place an acoustic transducer arrangement inside the external ear canal, such that its output face forms acoustic contact (using a gel or oil) with the outer walls of the external ear canal. The transducer arrangement is configured and positioned such that acoustic waves travel through the ear canal and are focused on the jugular vein bulb. This configuration may include phased array elements, or other elements that are arranged to be operated in any direction, phase or time delay. In order to determine precise location of the Jugular vein bulb, relative to the ear canal, the operator may rely on radiographic images acquired prior to operation of the imaging apparatus or on back reflected Doppler signals from the bulb. When using Doppler signals, the transducer arrangement, may include, inter alia, an acoustic transducer capable of generating and collecting acoustic signals having an appropriate frequency and duration for performing Doppler measurements (for example using ultrasound waves frequency of 2 MHz). A control unit analyzes these Doppler shifted signals to determine distance from probe head located in the ear canal to the Jugular vein bulb during the calibration mode, and also in between actual measurements to verify that the acoustic transducer has not shifted relative to the Jugular vein bulb.

Figure 4A:
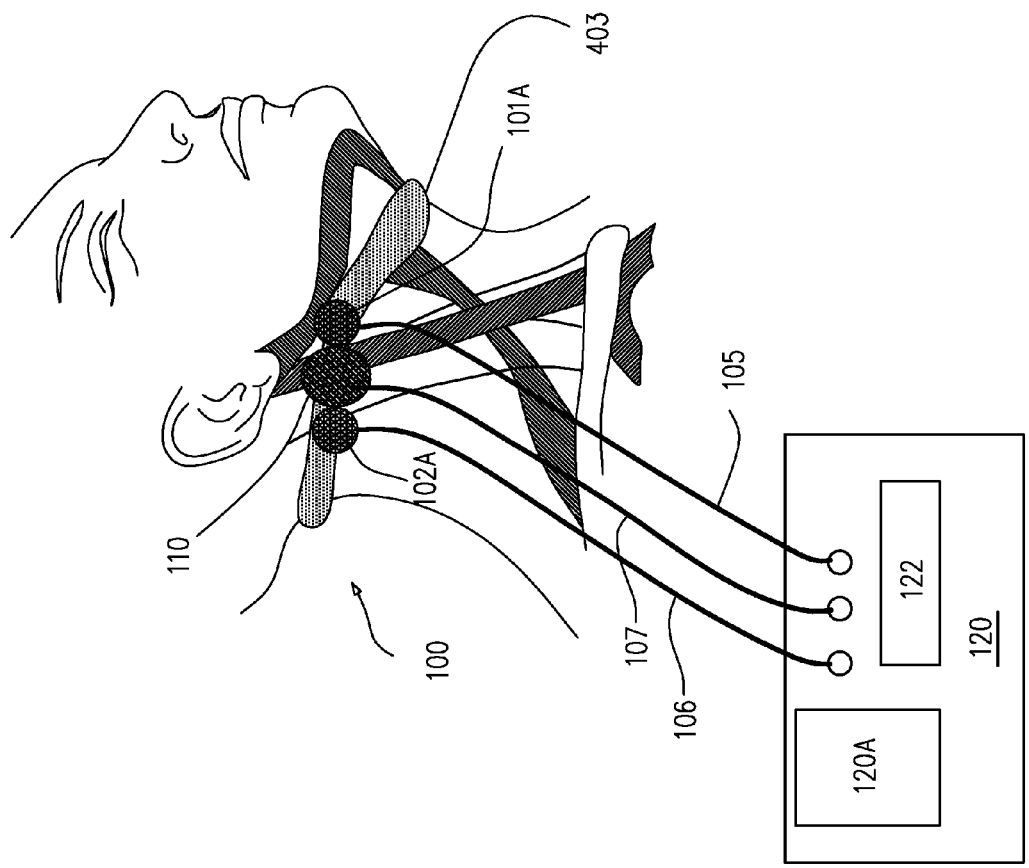
FIGS. 4A and 4B schematically illustrate two examples of the monitoring system configuration suitable for monitoring the oxygen saturation in the internal jugular vein of a human.
Figure 4B:
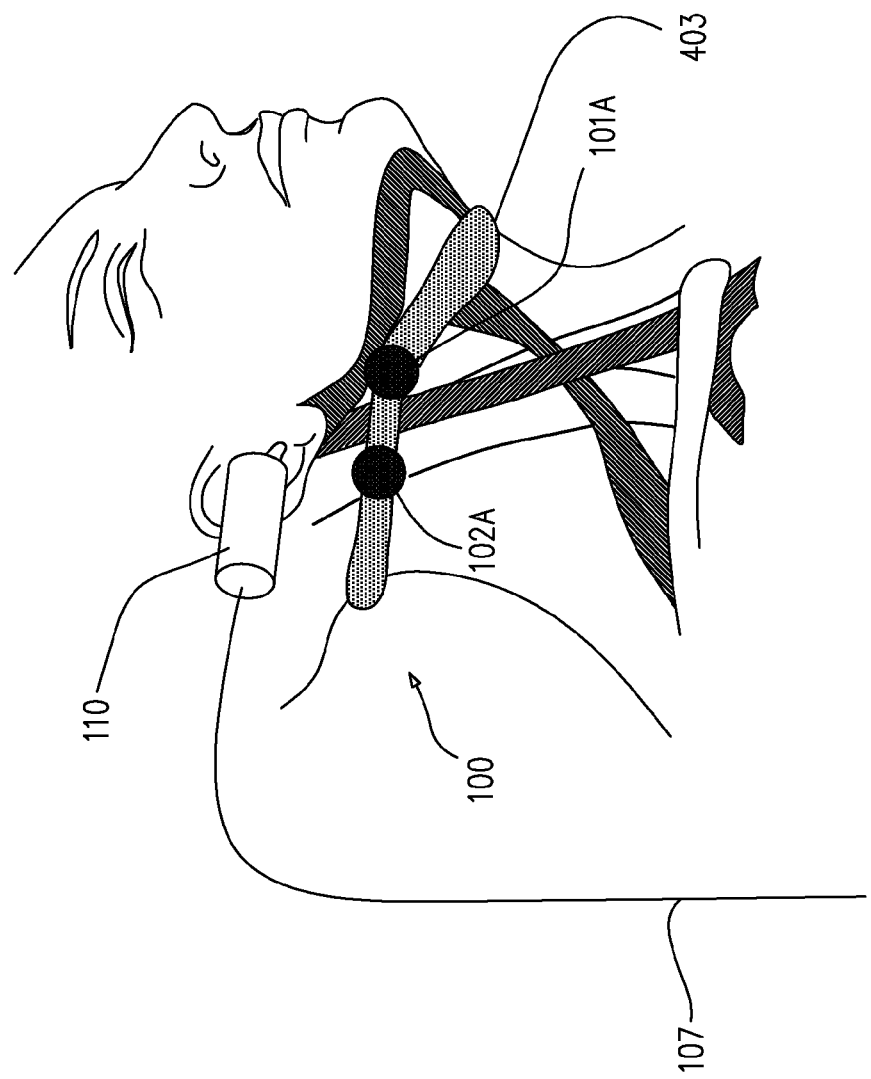

Reference is made to FIGS. 4A-4B exemplifying the use of a measurement system 100 of the present invention for measuring oxygen saturation level in a region of interest outside cerebral tissues. The region of interest is the internal jugular vein; in some cases the internal jugular vein bulb is located in the vicinity of the middle ear cavity. The region of interest is preferably located by using a Doppler imaging system capable of identifying blood flow direction and distance to vessel. Such a Doppler system may form part of a transducer arrangement 110 of measurement system 100. Once the location of the jugular vein region of interest is determined (either the bulb or another region), the transducer arrangement 110 is fixed in place using an adhesive that is extracted from underneath an acoustic output port or using a belt. A flexible probe (support structure) 403 is attached to the skin region overlaying the region of interest. The flexible probe 403 carries an illumination assembly 101A (at least light output ports thereof) and a detection assembly 102A (at least light input ports thereof) along with corresponding index matching optical adhesives for securing the positions of the input and output light ports. Flexible probe 403 is connected to a control unit 120 using cables, optical fibers or wireless means.

In the arrangement shown in FIG. 4A, transducer arrangement 110 is located such that at least its output port is on the support structure 403 in between light input and output ports. Control unit 120 operates to determine a distance between the input and output light ports such that light propagating through the region of interest is collected by the detection assembly 102A. In the system configuration of FIG. 4B, the transducer arrangement 110 is placed external to the support structure 403 in an optimal location for irradiating the jugular vein bulb or the jugular vein with acoustic radiation. Such an optimal location may be through the ear canal as disclosed above. The control unit (not shown here) then determines the optimal position of illumination and detection assemblies such that light scattered from the region of interest will reach the input port of the detection assembly 102A. The control unit controls the operation of the optical unit carried by the support structure 403 and the operation of the acoustic transducer arrangement so as to enable determination of the oxygen saturation of blood passing through the jugular vein. In addition, control unit may collect Doppler shifted acoustic signals being reflected from blood flowing inside the jugular vein to determine blood flow parameters as well as to adjust for movements or changes of the probe head relative to the region of interest.

It is understood by those skilled in the art that an acoustic transducer assembly can be inserted through other tracks or lumens inside the human body, such that it forms acoustic contact with an internal wall of the track.

According to yet another embodiment, one of the illumination or detection assemblies may be inserted through the same track or lumen as the transducer arrangement, or through a different track or lumen to provide optimal positioning of the system relative to the region of interest. Such a configuration may include a catheter inserted into a track or lumen or an endoscope carrying optical and acoustic means for imaging an internal part of the body.

It should also be noted that other blood vessels (veins or arteries) may be monitored using this apparatus, and the measurement technique is not limited to the jugular vein, given only as an example. Other examples include but are not limited to monitoring other blood analytes in blood vessels (such as glucose, urea and bilirubin) and monitoring other vessels (e.g. the femoral artery in the hip joint or at other locations where it is close to the skin). In each embodiment the blood vessel location is determined using an imaging system (preferably a Doppler imaging system) and the system of the present invention is used to monitor the blood vessel.

Reference is made to FIG. 5A exemplifying a modified probe (measurement unit) 101 for measuring in a region of interest. Here, an illumination assembly 101A includes one or more light emitter (not shown) and a light guiding unit including light guides, optical fibers or fiber bundles 810 and 814 optically coupled to each other by a coupler 850. Light from light emitter(s) is coupled into the fiber 810 at its one end, and propagates through this optical fiber towards the optical coupler 850 to be further coupled to optical fiber 814.

The distal end of fiber 814 presents a light output port OP of the illumination assembly. Also coupled to the optical coupler 850 is an optical fiber or fiber bundle 811. A detection assembly 102A includes one or more light detectors (not shown) and a light guiding unit including an optical fiber or fiber bundle 812 optically coupled to an optical fiber or fiber bundle 813 via an optical coupler 851, which is also coupled to the fiber or fiber bundle 811.

The optical coupler 850 is appropriately configured to couple a certain first portion (for example 1% of propagating light intensity) of input light propagating through fiber 810 to optical fiber 811, and coupling the other second portion of input light (e.g. 99%) into fiber 814. This second portion of light from fiber 814 illuminates, through light output port OP, a skin region 10 overlaying a region of interest 200. Fiber 813 delivers light, collected by light input port IP, towards the light detector(s).

Coupler 851 couples light from fiber 813 and fiber 811 into fiber 812. Coupler 851 is designed to provide maximal transmission of light from fiber 813 into fiber 812, meaning that there are minimal coupling losses. The coupling efficiency of coupler 851 from fiber 811 into fiber 812 should preferably be constant.

It should be understood that fiber portions 810 and 814 or fiber portions 813 and 812 can form the same physical fiber, and need not be separate fibers. It should also be understood that the optical unit (i.e., the length of the fiber portion 811 and the position of couplers 850 and 851 along fibers 810 and 813) is configured such that light traveling through fiber 811 is coherent with light, collected by input port IP and arriving at coupler 851, so as to satisfy the interference condition. This requirement is consistent with the requirement that the coherence length of the light source is longer than the path length of light inside the tissue, as explained above. Couplers 850 and 851 can be included in the flexible probe 403.

As photons 820 from fiber 811 interfere with tagged and untagged photons 250 propagating in fiber 813, the intensity of light reaching the detector(s) is modulated in time.

The interference signal of three electromagnetic fields is being detected by the detection assembly. It can be written as:

$$I_r(t) = C|E_U \exp[i(\omega_L t + \phi_U)] + E_T \exp[i((\omega_L + \Omega_{US})t + \phi_T)] + E_{LO} \exp[i(\omega_L t + \phi_{LO})]|^2 \quad [14]$$

wherein C is a proportionality constant depending on the efficiency of the detection assembly and area of the light input port, $E_U$ is the absolute amplitude of the untagged electromagnetic field and $E_T$ is the absolute amplitude of the tagged electromagnetic field, $\omega_L$ is the light frequency, $\phi_U$ and $\phi_T$ are the phases of the untagged and tagged electromagnetic fields respectively, $\Omega_{US}$ is the acoustic frequency, $E_{LO}$ is the absolute amplitude of the reference electromagnetic field and $\phi_{LO}$ is its phase.

The signal can be divided into three components:

$$I_1 = |E_U|^2 + |E_T|^2 + |E_{LO}|^2 + 2E_U E_{LO} \cos(\phi_U - \phi_{LO})$$

$$I_2 = 2E_{LO} E_T \cos(\Omega_{US} t + \phi_T - \phi_{LO})$$

$$I_3 = 2E_U E_T \cos(\Omega_{US} t + \phi_T - \phi_U) \quad [15]$$

The first component, $I_1$, will mostly be at DC and will have a certain linewidth that depends for example on the breathing rhythm of the body and on the Brownian motion of the scattering centers. The second and third interference patterns are time modulated at the frequency of acoustic waves 255 emitted by transducer arrangement 110. Control unit 120 analyzes the signal generated by the detection assembly to determine parameters of the region of interest and of the tissues surrounding the region of interest. All three components can be analyzed simultaneously. Additionally, each component can be separated by blocking transmission of photons 820, or of photons 250, or by analyzing the detected signals when the acoustic waves are not propagating (no "tagging").

For example, photons 820 can be used to determine light source characteristics by the control unit during the system operation. The control unit can activate coupler 851 to block transmission of light from fiber 813 into fiber 812 at specific time periods. During these periods, only photons 820 are detected, and can serve as a reference for the illuminating light properties (e.g. intensity, coherence length of source). According to another option, the control unit activates detection of photons 250, when acoustic waves 255 do not irradiate the tissues at all. Thus all of photons 250 are not tagged during these periods ("no tagging"). The signals detected during these periods result from the interference of untagged photons 250 and photons 820. This signal depends for example on the Brownian motion of the scattering centers, and on breathing rhythms. Thus, these two parameters can be determined during these periods, and be used to optimize the measurement conditions (for example to reduce artifacts from breathing). The control unit activates detection of photons 250 when acoustic waves 255 do irradiate the region of interest ("normal tagging"). When tagging occurs, there is an increase in components number two and three, relative to the periods of "no tagging". These relative changes can assist in determining parameters of the region of interest and of surrounding tissues.

According to yet another option, when acoustic radiation is used to tag the region of interest (normal tagging), the control unit can block collection of photons 820 by blocking their transmission through coupler 851, thereby sampling photons 250 (i.e. only the untagged light and the third component). This signal is used to decouple the contribution of $I_2$ to the signal modulated at the acoustic frequency (i.e. $I_2 + I_3$) when both photons 820 and 250 interfere (termed "coupled signal"), and thus extract the contribution of $I_3$.

In order to simultaneously decouple the contributions of $I_2$ and $I_3$ to the coupled signal, a frequency shift is preferably introduced in the reference arm formed by fiber 811.

Figure 5B:
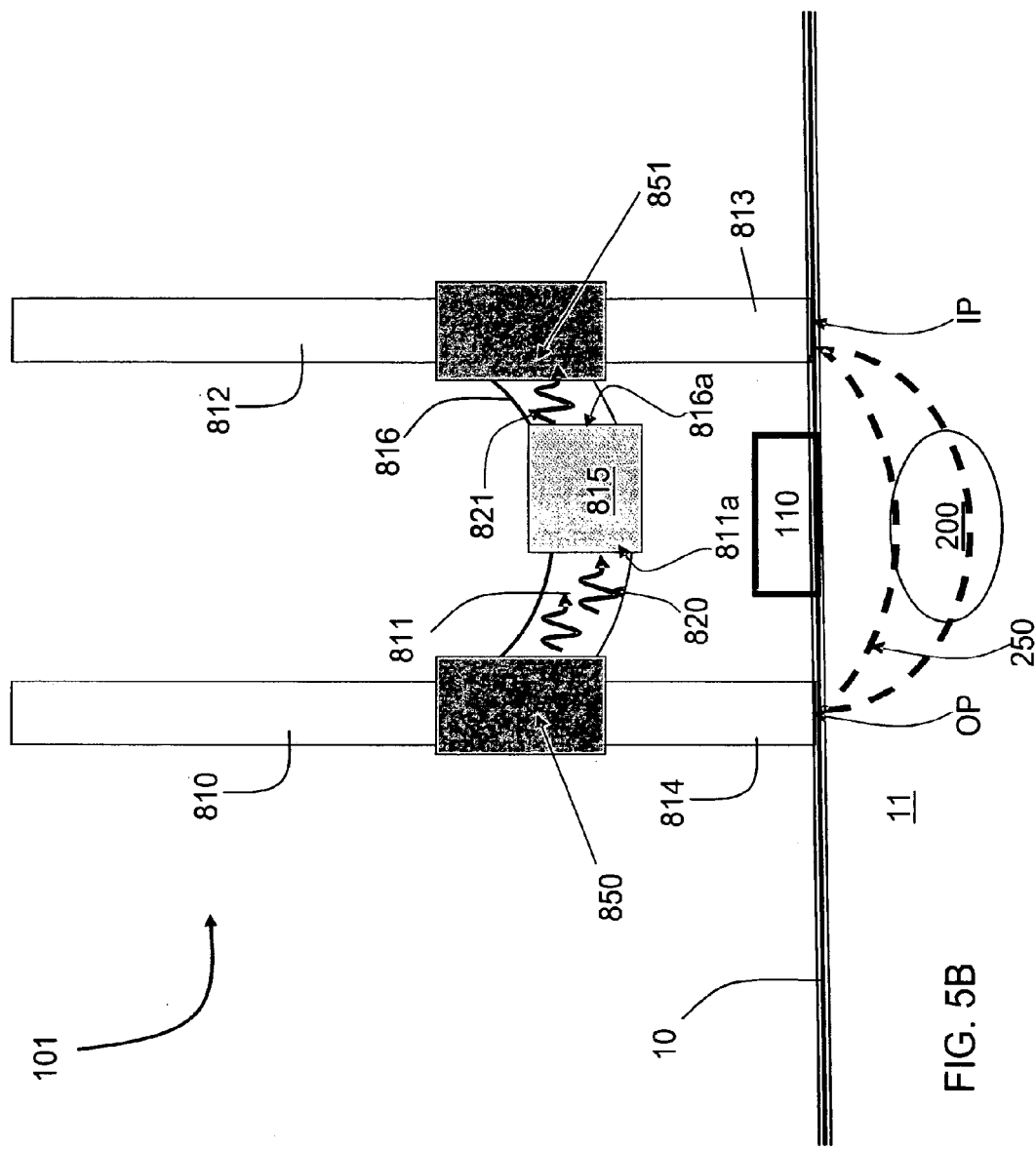

FIG. 5B illustrates a similar configuration of a measurement unit 101, but utilizing a light modulator (e.g., acousto-optic modulator or photorefractive crystal) 815 located in optical path of light passing through fiber 811. Light propagating through fiber 811 is coupled into this light modulator through its entry face 811a and is coupled out of the light modulator 815 through its exit face 816a into another optical fiber 816, which is in turn optically coupled to coupler 851. Coupler 851 couples light from optical fibers 816 and 813 into fiber 812. As light propagates through light modulator 815, its frequency is shifted by a certain frequency $\Omega_{AO}$ determined by a control unit (not shown) relative to the characteristic frequency $\Omega_{US}$ of acoustic radiation generated by a transducer arrangement 110. The modulation frequency $\Omega_{AO}$ is optimally chosen to be different from the characteristic frequency $\Omega_{US}$. Consequently, photons 820 are frequency shifted as they exit modulator 815, and are denoted modulated photons 821. As photons 250, collected at light input port IP and coupled by coupler 851 from fiber 813 to fiber 812, interfere with photons 821. The interference signal is:

$$I_t(t)=C|E_L\exp[i(\omega_L t+\phi_U)]+E_T\exp[i((\omega_L+\Omega_{US})t+\phi_U)]+ \\ E_{LO}\exp[i((\omega_L+\Omega_{AO})t+\phi_{LO})]|^2 \qquad [16]$$

and it has four relevant frequency components:

$$I'_1=|E_U|^2+|E_T|^2+|E_{LO}|^2$$

$$I'_2=2E_{LO}E_U\cos(\Omega_{AO}t+\phi_U-\phi_{LO})$$

$$I'_3=2E_{LO}E_T\cos((\Omega_{US}-\Omega_{AO})t+\phi_T-\phi_{LO})$$

$$I'_4=2E_TE_U\cos(\Omega_{US}t+\phi_T-\phi_U)$$

As the number of photons 821 can be monitored, for example by blocking transmission of photons 250 though coupler 851 and detecting the number of photons 821 reaching the detection unit, the contribution of the untagged photons to the first component $I'_1$, can be isolated, assuming, as before, $|E_U|^2 \gg |E_T|^2$. The generated signals at three different frequencies represent, respectively, interference between photons 821 and the untagged photons 250 ($I'_2$), interference between photons 821 and tagged photons 250 ($I'_3$), and interference of tagged and untagged photons 250 ($I'_4$). Since photons 821 do not pass through the body, the control unit can extract effects related to the overall light propagation in the body tissues from light source to detector, and local effects of the tagged volume separately.

For example, using the configuration of FIG. 5B, there are two independent measures for the tagged and untagged photons, allowing decoupling of speckle correlation or Brownian motion of the scattering centers, from components $I'_2$ and $I'_4$. In addition, once the tagged and untagged signals are decoupled, they can be used to calibrate tissue models A and B described above.

Thus, for example, the line width of component $I'_2$ can be used to determine the scattering coefficient of the tissues. Consequently, the scattering coefficient of tissue models A and B can be determined and used to calibrate and account for light propagation though surrounding tissues. Following, control unit 120 determines the absorption coefficient of the region of interest, decoupled from the scattering coefficient, by measuring the attenuation of light through the tissue.

In addition, the relative amplitudes of the components $I'_2$, $I'_3$ and $I'_4$ can be used to isolate the contribution of each signal. For example, the ratio between the amplitudes of components $I'_2$ and $I'_3$ can be used to optimize the modulation amplitude of component $I'_3$. This can be done by controlling the percentage of photons 820 that are coupled into fiber 811 by coupler 850, or by controlling the transfer efficiency of the modulator 815, resulting in a control over the number and phase of photons 821. The number of photons 821 can be made, for example, approximately equal to the number of tagged photons 250 at each wavelength by optimizing the amplitude of component $I'_3$. Once such a condition is achieved, component $I'_3$ will provide maximal sensitivity for changes in the tagged photons signal.

As the line width of the autocorrelation or power spectrum of the tagged signals, around the frequency of the acoustic radiation, is different when tagging is performed in different media, the control unit can determine, by monitoring the line width, when the ultrasound beam is used to optimally tag a volume of the region of interest.

Additionally or alternatively, other parameters of the tagged and untagged signals, such as amplitude and frequency, are used to determine one or more parameter indicative of a region of interest. For example, the blood volume in each location may be determined as described above. Control unit then displays the blood volume at each location being scanned by the acoustic beam. The display can be overlaid over a morphologic image of the organ being monitored, such as a CT or MRI image of the brain. The system of the present invention can monitor cerebral hemorrhage, subarachnoid hemorrhage or other blood clots in the brain. Alternatively, the oxygen saturation corresponding to each location of the acoustic beam can be determined and displayed. The system can be used to monitor tissue ischemia, in particular cerebral ischemia.

In another embodiment of the invention, the measurement system may be used to monitor changes in the concentration of analyte(s) in a region of interest during therapeutic or surgical procedures (such as during the application of high power ultrasound pulses or wave, laser ablation, or chemical procedures). For example, the transducer arrangement may be used for ablation of tumors or malformations in a tissue. During the application of high power ultrasound pulses, light is emitted and collected by illumination and detection assemblies, respectively, to determine the concentration of an analyte indicative of the treatment in the region being ablated. Alternatively, low power ultrasound pulses (that do not cause ablation) intermittently irradiate the region of interest, while low-power light pulses are emitted and collected by illumination and detection assemblies to determine the concentration of an analyte indicative of the treatment. For example, oxygenation of the region of interest is monitored. Such information is used for controlling and monitoring the treatment during application of ultrasound radiation.

It should be noted that same acoustic or light radiation applied for monitoring parameters of a region of interest, according to any embodiment of the present invention, can have therapeutic value. For example, acoustic radiation can improve thrombolitic activity of tPA (tissue Plasminogen Activator) or other thrombolitic agents. Therefore, the same acoustic radiation emitted by acoustic arrangement 110 having at least on of the following parameters: the same intensity, amplitude, duration, frequency, repetition rate, phase or power, used for monitoring tissue parameters such as oxygenation, may also provide therapy to the region of interest.

Figure 6A:
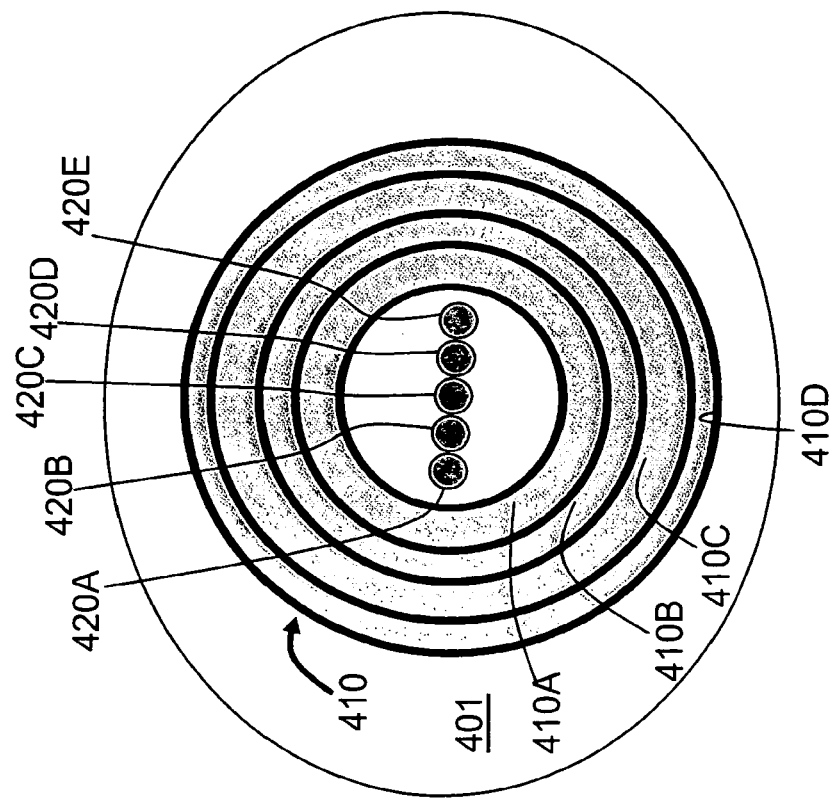
FIGS. 6A and 6B schematically illustrate two examples of configuration of a measurement unit suitable to be used in the system of the invention utilizing a phased array acoustic transducer arrangement.
Figure 6B:
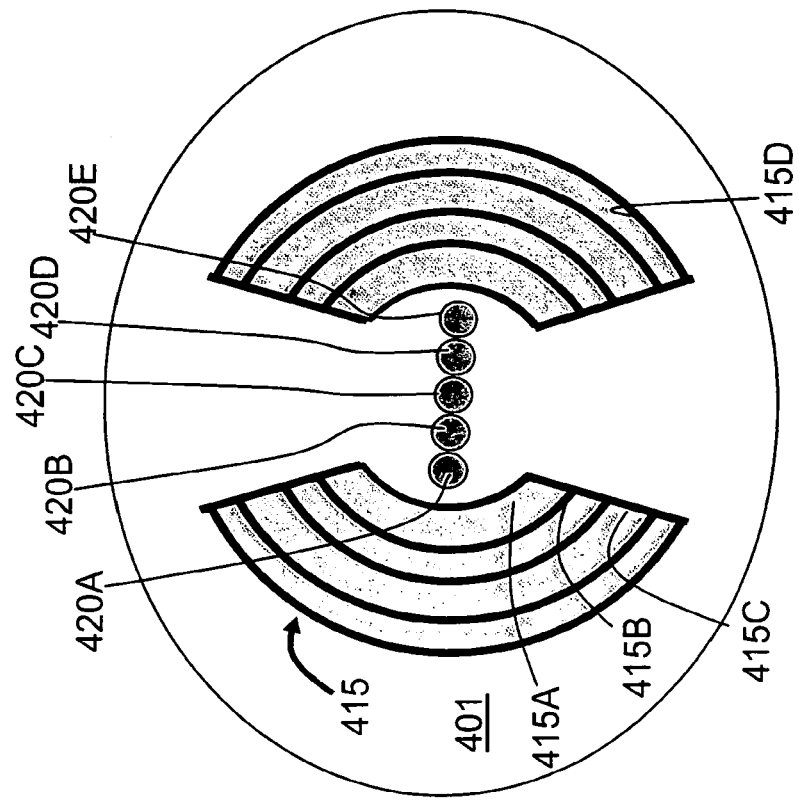

Reference is made to FIGS. 6A-6B exemplifying specific designs suitable for a transducer arrangement 110. In order to create a focused ultrasound beam, a phased array 410 comprising a plurality of elements is used. Different configurations of a phased array having a large effective area without compromising the flexibility for positioning the illumination and detection assemblies are described.

FIG. 6A schematically shows a top view of transducer arrangement 410 comprising an annular phased array, arranged to define a central opening. The number and dimensions of annular acoustic elements 410A-410D are determined to correspond to a predetermined focal depth and F# for the array. Transducer arrangement 410 is placed in acoustic contact with skin 401, overlaying a region of interest. Optical elements, preferably optical fibers, associated with illumination and detection assemblies are positioned inside the circular opening of the transducer arrangement. Five such elements 420A-420E are shown in the FIG. 6A figure. Any one of these elements can serve as an input or output light port according to an embodiment of the present invention. Such a configuration allows for a tighter focused beam and a shallower focal depth than those achievable with a single element transducer, or a phased array being placed in between the input and output light ports. The phased array elements 410A-410D are activated by a control unit (not shown here) to provide a focused ultrasound beam at the region of interest, or outside the region of interest. The focal plane of the phase array can be scanned by introducing corresponding delays between the activation of each annular element.

In the example of FIG. 6B, a partial annular phased array 415 is presented. Array 415 is designed generally similarly to the above-described array 410, and distinguishes from array 410 in that acoustic transducers 415A-415A do not form closed annular elements, but are only partially concave. Array 415 has similar focal depth and F# as the above-described array 410 (assuming these arrays have the same number of transducer elements and dimensions). Comparing the array design 415 to array 410, the array 415 provides more flexibility in positioning over skin areas which is required for example in the presence of a bone underneath skin region 401.

Reference is made to FIGS. 7A-7B and 8A-8B exemplifying different configurations of a support structure (probe) 403 suitable to be used in the present invention. In the example of FIGS. 7A-7B, the flexible probe 403 includes a flexible support 301, for example made of electrically insulating material(s), carrying light ports 303-316 (fiber-ends in appropriate housing, or light sources and/or light detectors as described above) and an acoustic output port 302 (or acoustic transducer arrangement). FIG. 7A is a bottom view of the flexible probe 403 viewed from the side by which it is attachable to a skin, and FIG. 7B shows a side view diagram of the flexible probe 403.

Optical fibers or electric wires 330-336 and 340-346 connect the light ports 310-316 and 303-309, respectively, to a common connector 320. An insulated electric cable (or acoustic waveguides) connects the acoustic output port 302 to the same connector 320. The acoustic port 302 is preferably coupled to an acoustic transducer arrangement 327 connected to the flexible support 301 using vibration controlling elements. The connector 320 is associated with a control unit (not shown), namely, couples the optical fibers and cables attached to the flexible support 301 with optical fibers and electric cables coupled to the control unit. The connector 320 may be composed of several connector elements. An adhesive 325 is attached to the bottom side of the support 301, such that the probe 403 can be fixed to the skin using this adhesive 325. Adhesive 325 is preferably light transparent and produces minimal scattering in a wavelength range used for measurements (i.e., emitted by light sources). Alternatively or additionally, the adhesive 325 may form an optical index matching layer between the light ports and the skin. Alternatively, the adhesive 325 may not cover the light ports at all, or may partially cover them. The adhesive 325 may contain pigments, chromophores or other materials for controlling the transmission of different wavelengths of light. An adhesive gel 326 is located below the acoustic port 302. The adhesive gel 326 is made from the same or different material as the adhesive 325 and is designed for optimal acoustic coupling between the acoustic port 302 and the skin. Possible materials for adhesives 325 and 326 include hydrogel based adhesives.

The different elements of the flexible probe 603 may be assembled in different ways. For example, the complete probe 603 is assembled prior to operation, and a user only needs to remove a thin layer covering the bottom side of adhesives 325 and 326. In yet another example, the adhesive 326 is attached to the acoustic output port 302 (preferably including the acoustic transducer arrangement itself) which is not attached to the probe 403 prior to the device operation. The user first attaches the flexible support 301 to the skin using the adhesive 325, and then inserts the acoustic port 302 through an appropriately provided opening in the support 301, where the transducer 327 is optionally connected to the support 301 using conventional means and is attached to the skin using the adhesive 326. The latter may be part of adhesive 325, and only the acoustic output port 302 is inserted and attached to the upper part of the adhesive 326 (being a double sided adhesive). The user first attaches the adhesives 325 and 326 to skin, then attaches the acoustic port 302 to the adhesive 326, and then connects the support 301 to the upper side of the adhesive 325 (being a double sided adhesive). Finally, the connector 320 is connected to the cables and fibers from the control unit to allow the operation of the probe. Each element of the flexible probe 403 and the complete probe 403 as a unit may be used only once and then discarded (i.e., is disposable), or used multiple times.

FIGS. 8A and 8B show, respectively, bottom and side views of a probe 403 in which a support 301 carries light ports (or light sources) and several acoustic ports 302, 319 and 319A (or acoustic transducer arrangements). Each of the acoustic ports 302, 319 and 319A is coupled to a connector 320 using cables 338, 339 and 339A, respectively. Adhesive gels 326, 329 and 329A are used to couple the acoustic ports 302, 319 and 319A, respectively, to the skin. Similarly, each of the acoustic ports may be separated from the probe 403 when not in use, and inserted by user for as preparation for operation.

Those skilled in the art will readily appreciate that various modifications and changes may be applied to the embodiments of the invention as hereinbefore described without departing from its scope defined in and by the appended claims.

The invention claimed is:

1. Apparatus comprising a measurement system adapted to perform non-invasive measurements on a subject's body, the measurement system comprising:
   a measurement unit comprising:
      an acoustic unit configured to direct acoustic radiation toward a region of interest within the subject's body; and
      an optical unit comprising:
         an illumination assembly that comprises at least one light emitter, and at least one first light guiding unit and at least one second light guiding unit,
            the at least one light emitter, the at least one first light guiding unit and the at least one second light guiding unit being optically coupled to each other via a first optical coupler; and
         a light detection assembly that comprises at least one light detector, the at least one second light guiding unit, and at least one third light guiding unit,
            the at least one light detector, the at least one second light guiding unit, and the at least one third light guiding unit being optically coupled to each other via a second optical coupler,
      the measurement unit being configured to provide a first operating condition such that:
         the acoustic unit directs acoustic radiation toward a region of interest within the subject's body,
         a first light portion is transmitted from the at least one light emitter to the at least one light detector, by being transmitted along the at least one second light guiding unit, from the first optical coupler to the second optical coupler, without passing through tissue of the subject's body, and
         a second light portion is transmitted from the at least one light emitter to the at least one light detector, by being transmitted from the at least one first light guiding unit to the at least one third light guiding unit via the region of interest within the subject's body, such that scattered light of the second light portion that passes into the at least one third light guiding unit contains a tagged component corresponding to photons tagged by the acoustic radiation, and an untagged component corresponding to photons untagged by the acoustic radiation, and a control unit configured to decouple, from each other, the tagged component and the untagged component of the second light portion received at the at least one light detector, based upon an interaction between light of the first light portion and light of the second light portion received at the at least one light detector.

2. The apparatus according to claim 1, wherein the at least one first light guiding unit, the at least one second light guiding unit, and the at least one third light guiding unit comprise, respectively, first, second and third optical fibers.

3. The apparatus according to claim 1, wherein the at least one first light guiding unit, the at least one second light guiding unit, and the at least one third light guiding unit comprise, respectively, first, second, and third optical fiber bundles.

4. The apparatus according to claim 1, wherein the measurement unit is configured to provide the first operating condition, by providing an operating condition such that light of the first light portion is coherent with light of the second light portion.

5. The apparatus according to claim 1, wherein:
the measurement unit is configured to further provide a second operating condition such that the second optical coupler blocks the second light portion from arriving at the at least one light detector by blocking light that is transmitted via the at least one third light guiding unit, and
the control unit is configured to determine a parameter of light emitted by the at least one light emitter, by analyzing light of the first light portion that was received at the at least one light detector, while the measurement unit provided the second operating condition.

6. The apparatus according to claim 1, wherein:
the measurement unit is configured to further provide a second operating condition such that:
the acoustic unit does not direct acoustic radiation toward the region of interest within the subject's body,
the first light portion is transmitted from the at least one light emitter to the at least one light detector by being transmitted along the at least one second light guiding unit from the first optical coupler to the second optical coupler without passing through tissue of the subject's body, and
the second light portion is transmitted from the at least one light emitter to the at least one light detector by being transmitted from the at least one first light guiding unit to the at least one third light guiding unit via the region of interest within the subject's body, such that scattered light of the second light portion that passes into the at least one third light guiding unit contains photons untagged by the acoustic radiation, and does not contain photons that were tagged by the acoustic radiation, and
the control unit is configured to determine a property of the tissue of the region of interest, based upon comparing light received at the at least one light detector while the measurement unit operates at the first operating condition to light received at the detector while the measurement unit operates at the second operating condition.

7. The apparatus according to claim 1, wherein:
the measurement unit is configured to provide a second operating condition such that the second optical coupler is configured to block the first light portion from arriving at the at least one light detector by blocking light that is transmitted via the at least one second light guiding unit, and
the control unit is configured to:
analyze light that was received at the at least one light detector, while the light of the first light portion was blocked from arriving at the at least one light detector, and
in response thereto, decouple a contribution of the first light portion from an interference pattern that was detected at the at least one light detector, while the measurement unit was providing the first operating condition.

8. The apparatus according to claim 1, further comprising a light modulator configured to be disposed along an optical path along the second light guiding portion and to shift a frequency of light of the first light portion that passes through the light modulator, such that photons of the first light portion that are received at the at least one light detector are frequency modulated with respect to a frequency of the photons when the photons were emitted from the at least one light emitter.

9. The apparatus according to claim 8, wherein the at least one second light guiding unit comprises at least one first optical fiber configured to guide light from the first optical coupler to an entry face of the light modulator, and at least one second optical fiber configured to guide light from an exit face of the light modulator to the second optical coupler.

10. The apparatus according to claim 8, wherein the light modulator is configured to shift the frequency of photons of the first light portion by a first frequency shift, and wherein the acoustic radiation is configured to shift a frequency of the tagged photons of the second light portion by a second frequency shift, the first and second frequency shifts being different from one another.

11. The apparatus according to claim 8, wherein:
by operating at the first operating condition, the measurement unit is configured to generate an interference pattern at the at least one light detector based upon an interaction of the tagged photons of the second light portion, the untagged photons of the second light portion, and the frequency-modulated photons of the first light portion, and
wherein the control unit is configured to determine a property of the tissue of the region of interest based upon analyzing relative amplitudes of respective components of the interference pattern.

12. The apparatus according to claim 8, wherein the measurement unit is configured to operate at the first operating condition by controlling a ratio between a number of photons in the first light portion and a number of tagged photons in the second light portion.

13. A method for performing non-invasive measurements on a subject's body, the method comprising:
directing acoustic radiation toward a region of interest within the subject's body;
transmitting light from a light emitter to a light detector under a first operating condition, such that:
a first light portion is transmitted from the light emitter to the light detector without passing through tissue of the subject,
a second light portion is transmitted from the light emitter to the light detector via the region of interest within the subject's body, such that scattered light of the second light portion that is received at the light detector contains a tagged component corresponding to photons tagged by the acoustic radiation, and an untagged component corresponding to photons untagged by the acoustic radiation, transmitted light of the first light portion is optically coupled to transmitted light of the second light portion, and light of the first light portion undergoes an interaction with received light of the second light portion at the light detector, by light of the first light portion that is received at the light detector and light of the second light portion that is received at the light detector being optically coupled to each other;

detecting the light received at the light detector; and decoupling from each other the tagged and untagged components of the second light portion received at the light detector, based upon the interaction between the light of the first light portion that is received at the light detector and the light of the second light portion that is received at the light detector.

14. The method according to claim 13, wherein transmitting light from the light emitter to the light detector comprises transmitting light through optical fibers.

15. The method according to claim 13, wherein transmitting light from the light emitter to the light detector comprises transmitting light through optical fiber bundles.

16. The method according to claim 13, wherein transmitting light from the light emitter to the light detector comprises transmitting light from the light emitter to the light detector such that light of the first light portion is coherent with light of the second light portion.

17. The method according to claim 13, further comprising:

transmitting light from the light emitter to the light detector under a second operating condition, by blocking the second light portion from arriving at the light detector, and determining a parameter of light emitted by the light emitter, by analyzing light of the first light portion that was received at the light detector, while the second light portion was blocked.

18. The method according to claim 14, further comprising:

transmitting light from the light emitter to the light detector under a second operating condition, while the acoustic radiation is not being directed toward the region of interest, such that:

the first light portion is transmitted from the light emitter to the light detector without passing through tissue of the subject, and the second light portion is transmitted from the light emitter to the light detector via the region of interest within the subject's body, such that scattered light of the second light portion that is received at the light detector contains photons untagged by the acoustic radiation, and does not contain photons that were tagged by the acoustic radiation, and determining a property of tissue of the region of interest based upon comparing light received at the light detector while light is transmitted from the light emitter to the light detector at the first operating condition, to light received at the detector while light is transmitted from the light emitter to the light detector at the second operating condition.

19. The method according to claim 13, further comprising:

transmitting light from the light emitter to the light detector under a second operating condition, by blocking the first light portion from arriving at the light detector, analyzing light that was received at the light detector, while the first light portion was blocked from arriving at the light detector, and in response thereto, decoupling a contribution of the first light portion from an interference pattern that was detected at the light detector due to the interaction of the first and second light portions, while the light is transmitted from the light emitter to the light detector under the first operating condition.

20. The method according to claim 13, further comprising shifting a frequency of light of the first light portion, such that photons of the first light portion that are received at the light detector are frequency modulated with respect to a frequency of the photons when the photons were emitted from the light emitter.

21. The method according to claim 20, wherein:

shifting the frequency of light of the first light portion comprises shifting the frequency of photons of the first light portion by a first frequency shift, and directing the acoustic radiation toward the region of interest comprises shifting a frequency of the tagged photons of the second light portion by a second frequency shift, the first and second frequency shifts being different from one another.

22. The method according to claim 20, wherein transmitting light from the light emitter to the light detector under the first operating condition comprises generating an interference pattern at the light detector based upon an interaction of the tagged photons of the second light portion, the untagged photons of the second light portion, and the frequency-modulated photons of the first light portion, the method further comprising determining a property of tissue of the region of interest based upon analyzing relative amplitudes of respective components of the interference pattern.

23. The method according to claim 20, wherein transmitting light from the light emitter to the light detector under the first operating condition, comprises controlling a ratio between a number of photons in the first light portion and a number of tagged photons in the second light portion.

* * * * *